United States Patent
Wang et al.

(10) Patent No.: US 9,499,530 B2
(45) Date of Patent: Nov. 22, 2016

(54) QUINAZOLINE DERIVATIVE, COMPOSITION HAVING THE DERIVATIVE, AND USE OF THE DERIVATIVE IN PREPARING MEDICAMENT

(75) Inventors: Shulong Wang, Hangzhou (CN); Jian Cai, Hangzhou (CN); Qiufu Ge, Hangzhou (CN); Dianwu Guo, Hangzhou (CN); Lan Yang, Hangzhou (CN); Binnan Huang, Hangzhou (CN); Zhenhua Liu, Hangzhou (CN); Zhonghua Peng, Hangzhou (CN); Ximing Shen, Hangzhou (CN); Feiyu Feng, Hangzhou (CN)

(73) Assignees: HANGZHOU MINSHENG INSTITUTES FOR PHARMA RESEARCH, Hangzhou, Zhejiang (CN); HANGZHOU MINSHENG PHARMACEUTICAL CO. LTD, Hangzhou, Zhejiang (CN)

( * ) Notice: Subject to any disclaimer, the term of this patent is extended or adjusted under 35 U.S.C. 154(b) by 125 days.

(21) Appl. No.: 14/234,326

(22) PCT Filed: Jul. 21, 2012

(86) PCT No.: PCT/CN2012/079439
§ 371 (c)(1),
(2), (4) Date: Sep. 8, 2014

(87) PCT Pub. No.: WO2013/017073
PCT Pub. Date: Feb. 7, 2013

(65) Prior Publication Data
US 2015/0080392 A1    Mar. 19, 2015

(30) Foreign Application Priority Data

Aug. 1, 2011 (CN) .......................... 2011 1 0218027
May 28, 2012 (CN) .......................... 2012 1 0174828

(51) Int. Cl.
| | | |
|---|---|---|
| C07D 417/04 | (2006.01) | |
| C07D 405/14 | (2006.01) | |
| C07D 405/04 | (2006.01) | |
| C07D 403/14 | (2006.01) | |

(52) U.S. Cl.
CPC ........... *C07D 417/04* (2013.01); *C07D 403/14* (2013.01); *C07D 405/04* (2013.01); *C07D 405/14* (2013.01)

(58) Field of Classification Search
CPC . C07D 417/04; C07D 405/04; C07D 403/14
See application file for complete search history.

(56) References Cited

U.S. PATENT DOCUMENTS

2012/0208833 A1* 8/2012 Wang ................... C07D 405/04
514/266.24

FOREIGN PATENT DOCUMENTS

| CN | 102108079 A | 6/2011 |
|---|---|---|
| GB | 2345486 A | 7/2000 |
| WO | 99/35146 A1 | 7/1999 |
| WO | 2008/033749 A2 | 3/2008 |
| WO | 2011/035540 A1 | 3/2011 |

OTHER PUBLICATIONS

Noolvi et al., A comparative QSAR analysis of quinazoline analogues as tyrosine kinase (erbB-2) inhibitors Medicinal Chemistry (2011), 7(3), 200-212.*
Banker et al. (1997).*
Vippagunta (2001).*
McMahon et al. (2000).*
Pinedo et al. (2000).*

* cited by examiner

*Primary Examiner* — Paul V Ward
(74) *Attorney, Agent, or Firm* — Novick, Kim & Lee, PLLC; Allen Xue

(57) ABSTRACT

A class of quinazoline derivatives or pharmaceutically acceptable salts or solvates thereof with novel structures is provided; meanwhile, a pharmaceutical composition comprising a pharmaceutically effective amount of said quinazoline derivatives or pharmaceutically acceptable salts or solvates thereof, and pharmaceutically acceptable excipients or additives is also provided. By modifying and transforming the quinazoline and screening of the transformed compounds on the activity of tyrosine kinase inhibition, most of the compounds have been found to possess inhibitory activity against one or several of EGFR, VEGFR-2, c-erbB-2, c-erbB-4, c-met, tie-2, PDGFR, c-src, lck, Zap70 and fyn kinases. The present invention has the advantages of reasonable design, broad source of and easy access to the raw materials, simple and easy operation of the preparation methods, mild reaction conditions, high yield of the products and being beneficial for industrial-scale production.

18 Claims, No Drawings

QUINAZOLINE DERIVATIVE, COMPOSITION HAVING THE DERIVATIVE, AND USE OF THE DERIVATIVE IN PREPARING MEDICAMENT

TECHNICAL FIELD

The present invention relates to quinazoline derivatives, compositions containing them and their pharmaceutical use, particularly their application in preparation of anti-tumor medicaments.

BACKGROUND ART

Cancer is a leading cause of death worldwide. According to statistics, 12 million people are diagnosed with cancer worldwide each year and 7.6 million people died as a result of cancer in 2008 (around 13% of all deaths). In 2010, it is reported on World Cancer Day that cancer accounts for an eighth of all death cases worldwide each year. Currently, in China there is between 1.8 million and 2 million incidence cases of cancer and between 1.4 million and 1.5 million cancer deaths annually.

Functional disorder of protein tyrosine kinases leads to a series of disease in living organisms. Data show that over 50% of proto-oncogenes and ocogene products have protein tyrosine kinase activity, and their abnormal expression would cause the disorder of the regulation of cell proliferation, and further leads to tumorigenesis. Furthermore, the abnormal expression of tyrosine kinases is also closely related to tumor invasion and metastasis, tumor angiogenesis, tumor resistance to chemotherapy. Effective inhibition of protein tyrosine kinases can achieve the purpose of tumor treatment. Protein tyrosine kinases have become a new target for anti-tumor medicant research. Protein tyrosine kinases can be divided into receptor protein tyrosine kinases (RPTKs) and non-receptor protein tyrosine kinases (nRPTKs). RPTKs are typically composed of an extracellular region, a transmembrane region, and an intracellular kinase region. According to the different structures of the extracellular region, RPTKs can be divided into the following main categories: (1) epidermal growth factor receptor (EGFR) family, the main members of the family including EGFR (HER1/erbB-1), HER2 (neu/erbB-2), HER3 (erbB-3), HER4 (erbB-4). The expression of human epidermal growth factor receptors (HERs) is enhanced in many tumors, such as colorectal cancer, head and neck squamous epithelial cell carcinoma, non-small cell lung cancer (NSCLC), breast cancer, pancreatic cancer, renal cell carcinoma; (2) vascular endothelial growth factor receptor (VEGFR), the main members of the family including VEGFR-1 (FLT-1), VEGFR-2 (KDR-FLK-1), VEGFR-3 (FLT-4), etc., which are important regulators in physiological or pathological angiogenesis; (3) platelet-derived growth factor receptor (PDGFR), the main members of the family including PDGFR-α, PDGFR-β, colony-stimulating factor 1 receptor (CSF-1R), FLK-2, stem cell factor receptor (c-kit), etc. Activation of the receptors is associated with tumors; (4) fibroblast growth factor receptor (FGFR), the main members of the family including FGFR-1, FGFR-2, FGFR-3, FGFR-4, etc. Such receptors are closely related to angiogenesis and tumorigenesis; (5) others, such as insulin receptor (INSR), hepatic cell growth factor receptor (HGFG), nerve growth factor receptor (HGFG), etc. (Jian Ding, "Protein tyrosine kinase—a promising anti-tumor target", Proceedings of the 3th Chinese Conference on Oncology, 2004, 11, 130-140). nRPTKs generally have no extracellular structure. They are usually coupled with cell membranes or present in cytoplasm, such as Src kinase family including Abl, Abl-Brc, etc. The activation of this large category of kinases frequently facilitate the development and progression of tumors. Various tyrosine kinases constitue intersectant and complex cellular signal transduction pathways, and the inhibition of the activity of a tyrosine kinase can often be compensated by the enhancement of the activity of one or more other kinases. Simultaneous inhibition of the activity of multiple tyrosine kinases is a new trend in the current development of this kind of anti-tumor medicaments.

Research has found that aberrant protein tyrosine kinase activity is also associated with other diseases, for example: psoriasis (Dvir, et al., Journal of Cell Biology, 1991, 113, 856-865), fibroid degeneration, atherosclerosis, restenosis (Buchdunger, et al., Proc. Natl. Acad. Sci. USA, 1991, 92, 2258-2262), autoimmune diseases, allergies, asthma, transplant rejection (Klauser and Samelson, Cell, 1991, 64, 875-878), inflammation (Berkois, Blood, 1992, 79(9), 2446-2454), thrombogenesis (Salari, et al., FEBS, 1990, 263(1), 104-108) and nervous system diseases (Ohmichi, et al., Biochemistry, 1992, 31, 4034-4039).

Therefore, it is undoubtedly and extremely advantageous in the treatment of tumor growth, proliferation and other related diseases to choose medicaments, which be able to effectively inhibit overactivity and/or overexpression of tyrosine kinases. Currently, a new class of anti-tumor medicaments acting on tyrosine kinases include imatinib mesylate, gefitinib, erlotinib, sorafenib, dasatinib, lapatinib, and so on.

DETAILED DESCRIPTION OF THE INVENTION

An object of the invention is to provide stable, safe and effective quinazoline derivatives, to synthesize and screen a series of new compounds being able to effectively inhibit the activities of multiple tyrosine kinases, exhibit good anti-tumor effect in vivo, and can be used for the treatment of tumor diseases.

Another object of this invention is to provide quinazoline derivatives which are suitable for treatment of other diseases mediated by protein tyrosine kinases, for example, for prevention and treatment of diseases, such as psoriasis, fibroid degeneration, atherosclerosis, restenosis, autoimmune diseases, allergies, asthma, transplant rejection, inflammation diseases, thrombogenesis and nervous system diseases.

The invention is realized by the following technical solutions.

This invention provides quinazoline derivatives or pharmaceutically acceptable salts or solvates thereof having the following structural general formula (I):

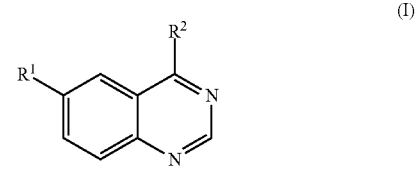

in the formula, $R^1$ is

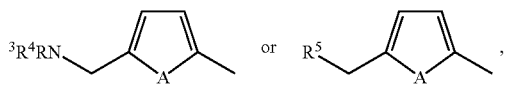

A is O, S, $NR^7$, wherein $R^7$ is H or $C_{1-6}$ alkyl;
$R^2$ is

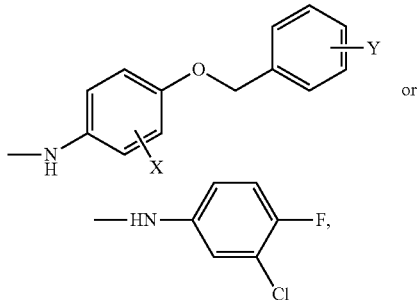

X is halogen, preferably fluoro, chloro or bromo, Y is halogen, preferably fluoro, chloro or bromo;

$R^3$ and $R^4$ are each independently selected from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

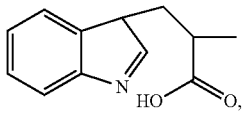

wherein said substituents are one or more groups selected from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, optionally substituted heteroaryl $C_{1-6}$ alkoxy, said substituent on the aryl or heteroaryl group is one or more group selected from hydroxy, mercapto, amino, nitro, halogen, $C_{1-6}$ alkyl, $C_{1-6}$ alkoxy, $C_{1-6}$ alkylthio, carboxy.

$R^5$ is a 3- to 8-membered heterocyclic group containing at least one heteroatom selected from N, O, S, which is optionally substituted by $R^6$, wherein said $R^6$ is selected from H or $C_{1-6}$ alkyl, halo $C_{1-6}$ alkyl, hydroxy $C_{1-6}$ alkyl.

But the following compounds are not included:
N-(4-(3-fluorobenzyloxy)-3-chlorophenyl)-6-(5-(morpholinyl-methyl)-2-furyl)quinazolin-4-amine;
N-(4-(3-fluorobenzyloxy)-3-chlorophenyl)-6-(5-(4-methylpiperazinyl-1-methyl)-2-furyl)-quinazolin-4-amine;
N-(4-(3-fluorobenzyloxy)-3-chlorophenyl)-6-(5-(piperazinyl-1-methyl)-2-furyl)quinazolin-4-amine; and
N-(4-(3-fluorobenzyloxy)-3-chlorophenyl)-6-(5-((2-(methylthio)ethylamino)methyl-2-furyl)quinazolin-4-amine.

In preferred technical solutions of this invention, in the inventive quinazoline derivatives or pharmaceutically acceptable salts or solvates thereof, $R^1$ is

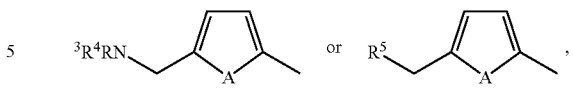

A is O, S, $NR^7$, wherein $R^7$ is H or $C_{1-6}$ alkyl;
$R^2$ is

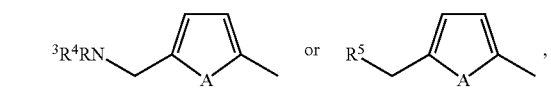

X is fluoro, chloro or bromo, Y is fluoro, chloro or bromo;

$R^3$ and $R^4$ are each independently selected from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

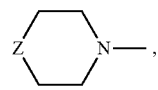

wherein said substituents are one or more groups selected from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, $C_{2-6}$ alkenoxycarbonyl, $C_{2-6}$ alkenoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, optionally substituted heteroaryl $C_{1-6}$ alkoxy, said substituent on the aryl or heteroaryl group is one or more group selected from hydroxy, mercapto, amino, nitro, halogen, $C_{1-6}$ alkyl, $C_{1-6}$ alkoxy, $C_{1-6}$ alkylthio, carboxy.

$R^5$ is

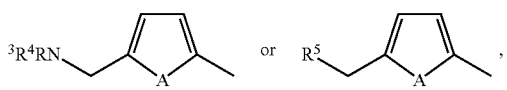

in which Z is S, O or $NR^6$, wherein said $R^6$ is selected from H or $C_{1-6}$ alkyl.

According to further preferred technical solutions of this invention, in said general formula (I), in which $R^1$ is

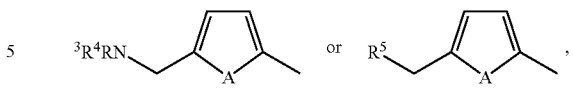

A is O, S, $NR^7$, wherein $R^7$ is H or $C_{1-6}$ alkyl;

$R^2$ is

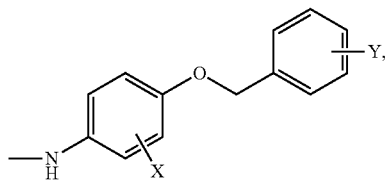

wherein X is fluoro, chloro or bromo, Y is fluoro, chloro or bromo;

$R^3$ is $C_{1-10}$ alkyl, $C_{2-10}$ unsaturated alkenyl, $C_{2-10}$ unsaturated alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

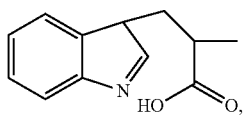

wherein said substituents are one or more groups selected from nitro, amino, carboxy, halogen atoms, hydroxy, mercapto, methoxy, amide group, ethoxycarbonyl, methoxycarbonyl, aminocarbonyl, optionally substituted phenyl, optionally substituted benzyl, optionally substituted benzyloxy, the substituent on phenyl group is one or more group selected from hydroxy, halogen, methoxy, nitro, and halogen is one selected from fluoro, chloro, bromo;

$R^4$ is H or $C_{1-6}$ alkyl, preferably $C_{1-4}$ alkyl;

$R^5$ is

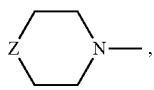

in which Z is S, O or $NR^6$, wherein said $R^6$ is selected from H or $C_{1-6}$ alkyl.

According to the preferred technical solutions of the present invention, in structural general formula (I), $R^1$ is

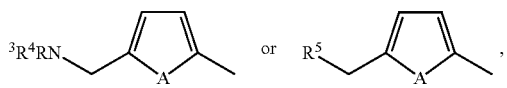

A is O, S, $NR^7$, wherein $R^7$ is H or $C_{1-6}$ alkyl;

$R^2$ is

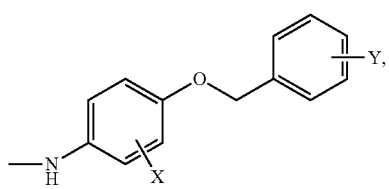

wherein X is chloro, Y is fluoro;

$R^3$ is $C_{1-10}$ alkyl, $C_{2-10}$ alkenyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, or

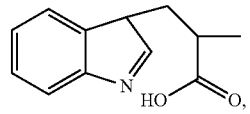

wherein the substituent is one or more group selected from nitro, amino, carboxy, halogen, hydroxy, mercapto, methylthio, methoxy, ethoxycarbonyl, methoxycarbonyl, aminocarbonyl, optionally substituted phenyl, optionally substituted benzyl, optionally substituted benzyloxy, the substituent on phenyl group is one or more group selected from hydroxy, halogen, methoxy, nitro;

$R^4$ is H or $C_{1-4}$ alkyl; $R^5$ is

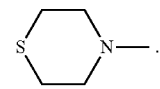

In preferred technical solutions of this invention, $R^3$ or $R^4$ can be linear or branched $C_{1-8}$ hydroxyalkyl, or $C_{2-10}$ hydroxyalkenyl, in which said hydroxy can mono- or polysubstitute on any carbon atom to form structural forms such as R—OH, R(R'—OH)—OH; meanwhile, the above-described one or more substituents selected from such as nitro, amino, carboxy, halogen atoms, hydroxy, mercapto, methylthio, methoxy, ethoxycarbonyl, methoxycarbonyl, aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryl $C_{1-6}$ alkoxy, optionally substituted heteroaryl $C_{1-6}$ alkoxy, can also be bonded to any carbon atom in alkyl esters and alkyl ethers. That is to say, these groups and hydroxy groups may substitute together in various combinations.

More preferably, said hydroxy group may be subjected to etherification or esterification reaction, therefore $R^3$ in the present invention can also a linear or branched, saturated or unsaturated $C_{1-8}$ alkyl ester or alkyl ether to form structural forms such as R—COOR' or R—OR', wherein R can be $C_{1-5}$ alkyl or $C_{2-5}$ alkenyl, and R' can be $C_{1-6}$ alkyl, $C_{2-6}$ alkenyl; Likewise, the above-described one or more substituents, such as nitro, amino, carboxy, halogen atoms, hydroxy, mercapto, methylthio, methoxy, ethoxycarbonyl, methoxycarbonyl, aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryl $C_{1-6}$ alkoxy, optionally substituted heteroaryl $C_{1-6}$ alkoxy, can also mono- or polysubstitute on any carbon atom in alkyl esters and alkyl ethers. For example, amino and hydroxy groups can be bonded to different carbon atoms in alkyl ester or alkyl ether, and amino group can also be bonded to multiple alkyl alcohols.

In preferred technical solutions, $R^3$ is selected from the following structures containing optical isomers thereof:

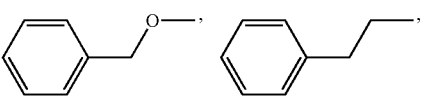

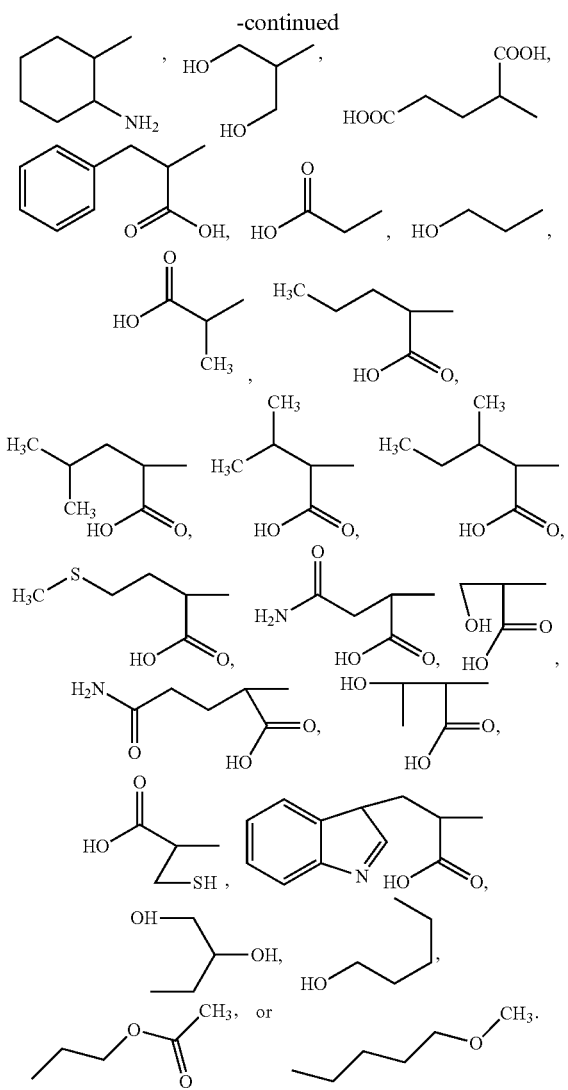

According to preferred technical solutions of this invention, said quinazoline derivatives of structural general formula (I) or pharmaceutically acceptable salts or solvates thereof are selected from the following compounds numbered MS1 to MS35:

Number MS1:
N-(3-chloro-4-[(3-fluorobenzyl)oxy)phenyl)-6-(5-((4-hydroxybutyl)amino)methyl-2-furyl)-4-quinazolinamine;
N-(3-chloro-4-((3-fluorobenzyl)oxy)phenyl)-6-(5-((3-phenylpropyl)amino)methyl)-2-furyl)-4-quinazolinamine;
Number MS2:
N-(3-chloro-4-((3-fluorobenzyl)oxy)phenyl)-6-(5-((n-hexylamino)methyl)-2-furyl)-4-quinazolinamine;
Number MS3:
N-(3-chloro-4-((3-fluorobenzyl)oxy)phenyl)-6-(5-((ethylamino)methyl)-2-furyl)-4-quinazolinamine;
Number MS4:
N-(3-chloro-4-((3-fluorobenzyl)oxy)phenyl)-6-(5-(N,N-diethylamino)methyl)-2-furyl)-4-quinazolinamine;
Number MS5:
N-(3-chloro-4-((3-fluorobenzyl)oxy)phenyl)-6-(5-(((2-butenyl)amino)methyl)-2-furyl)-4-quinazolinamine;
Number MS6:
N-(3-chloro-4-((3-fluorobenzyl)oxy)phenyl)-6-(5-((2-(1,3-dihydroxypropyl)amino)methyl)-2-furyl)-4-quinazolinamine;
Number MS7:
N-(3-chloro-4-((3-fluorobenzyl)oxy)phenyl)-6-((5-((cyclohexylmethyl)amino)methyl)-2-furyl)-4-quinazolinamine;
Number MS8:
N-(3-chloro-4-((3-fluorobenzyl)oxy)phenyl)-6-(5-(((2-(3-cyclohexenyl)ethyl)amino)methyl)-2-furyl)-4-quinazolinamine;
Number MS9:
N-(3-chloro-4-((3-fluorobenzyl)oxy)phenyl)-6-(5-((((3-chlorocyclohexyl)methyl)amino)methyl)-2-furyl)-4-quinazolinamine;
Number MS 10:
N-(3-chloro-4-((3-fluorobenzyl)oxy)phenyl)-6-(5-(((4-methoxybutyl)amino)methyl)-2-furyl)-4-quinazolinamine;
Number MS11:
N-(3-chloro-4-((3-fluorobenzyl)oxy)phenyl)-6-(5-(((3-chlorobenzyl)amino)methyl)-2-furyl)-4-quinazolinamine;
Number MS 12:
N-(3-chloro-4-((3-fluorobenzyl)oxy)phenyl)-6-(5-(((2-(4-nitrophenyl)ethyl)amino)methyl)-2-furyl)-4-quinazolinamine;
Number MS13:
N-(3-chloro-4-((3-fluorobenzyl)oxy)phenyl)-6-(5-(((2-(4-hydroxyphenyl)ethyl)amino)methyl)-2-furyl)-4-quinazolinamine;
Number MS 14:
N-(3-chloro-4-((3-fluorobenzyl)oxy)phenyl)-6-(5-(((2-(3,5-dimethoxyphenyl)ethylamino)methyl)-2-furyl)-4-quinazolinamine;
Number MS15:
N-(3-chloro-4-((3-fluorobenzyl)oxy)phenyl)-6-(5-(((2-(3-hydroxy-5-fluorophenyl)ethyl)amino)methyl)-2-furyl)-4-quinazolinamine;
Number MS 16:
N-(3-chloro-4-((3-fluorobenzyl)oxy)phenyl)-6-(5-(((2-(3-chloro-5-fluorophenyl)ethyl)amino)methyl)-2-furyl)-4-quinazolinamine;
Number MS 17:
N-(3-chloro-4-((3-fluorobenzyl)oxy)phenyl)-6-(5-(((2,6-dihydroxyhexyl)amino)methyl)-2-furyl)-4-quinazolinamine;
Number MS 18:
N-(3-chloro-4-((3-fluorobenzyl)oxy)phenyl)-6-(5-((bis(2-hydroxyethyl)amino)methyl)-2-furyl)-4-quinazolinamine;
N-(3-chloro-4-((3-fluorobenzyl)oxy)phenyl)-6-(5-(((1-carboxyethyl)amino)methyl)-2-furyl)-4-quinazolinamine;
N-(3-chloro-4-((3-fluorobenzyl)oxy)phenyl)-6-(5-(((1-carboxybutyl)amino)methyl)-2-furyl)-4-quinazolinamine;
N-(3-chloro-4-((3-fluorobenzyl)oxy)phenyl)-6-(5-(((1-carboxy-3-methylbutyl)amino)methyl)-2-furyl)-4-quinazolinamine;
N-(3-chloro-4-((3-fluorobenzyl)oxy)phenyl)-6-(5-(((1-carboxy-2-methylpropyl)amino)methyl)-2-furyl)-4-quinazolinamine;
N-(3-chloro-4-((3-fluorobenzyl)oxy)phenyl)-6-(5-(((1-carboxy-2-methylbutyl)amino)methyl)-2-furyl)-4-quinazolinamine;
N-(3-chloro-4-((3-fluorobenzyl)oxy)phenyl)-6-(5-(((1-carboxy-4-amino-4-oxobutyl)amino) methyl)-2-furyl)-4-quinazolinamine;

N-(3-chloro-4-((3-fluorobenzyl)oxy)phenyl)-6-(5-((((1-carboxy-2-hydroxypropyl)amino)methyl)-2-furyl)-4-quinazolinamine;
N-(3-chloro-4-((3-fluorobenzyl)oxy)phenyl)-6-(5-((((1-carboxy-3-(3H-indol-3-yl)propyl)amino)methyl)-2-furyl)-4-quinazolinamine;
Number MS 19:
N-(3-chloro-4-((3-fluorobenzyl)oxy)phenyl)-6-(5-(((benzyloxy)amino)methyl)-2-furyl)-4-quinazolinamine;
Number MS20:
N-(3-chloro-4-((3-fluorobenzyl)oxy)phenyl)-6-(5-(((2-(3-chlorophenyl)ethyl)amino)methyl)-2-furyl)-4-quinazolinamine;
Number MS21:
N-(3-chloro-4-((3-fluorobenzyl)oxy)phenyl)-6-(5-(((3-aminocyclohexyl)amino)methyl)-2-furyl)-4-quinazolinamine;
Number MS22:
N-(3-chloro-4-((3-fluorobenzyl)oxy)phenyl)-6-(5-(((carboxymethyl)amino)methyl)-2-furyl)-4-quinazolinamine;
Number MS23:
N-(3-chloro-4-((3-fluorobenzyl)oxy)phenyl)-6-(5-(((1,3-dicarboxypropyl)amino)methyl)-2-furyl)-4-quinazolinamine;
Number MS24:
N-(3-chloro-4-((3-fluorobenzyl)oxy)phenyl)-6-(5-((((1-carboxy-2-phenyl)ethyl)amino)methyl)-2-furyl)-4-quinazolinamine;
Number MS25:
N-(3-chloro-4-((3-fluorobenzyl)oxy)phenyl)-6-(5-(((2-carboxypropyl)amino)methyl)-2-furyl)-4-quinazolinamine;
Number MS26:
N-(3-chloro-4-((3-fluorobenzyl)oxy)phenyl)-6-(5-((((1-carboxy-3-methylthio)propyl)amino) methyl)-2-furyl)-4-quinazolinamine;
Number MS27:
N-(3-chloro-4-((3-fluorobenzyl)oxy)phenyl)-6-(5-(((2-hydroxyethyl)amino)methyl)-2-furyl)-4-quinazolinamine;
Number MS28:
N-(3-chloro-4-((3-fluorobenzyl)oxy)phenyl)-6-(5-((((1-carboxy-2-hydroxy)ethyl)amino)methyl)-2-furyl)-4-quinazolinamine;
Number MS29:
N-(3-chloro-4-((3-fluorobenzyl)oxy)phenyl)-6-(5-(((1-carboxy-2-mercapto)ethyl)amino)methyl)-2-furyl)-4-quinazolinamine;
Number MS30:
N-(3-chloro-4-((3-fluorobenzyl)oxy)phenyl)-6-(5-((((1-carboxy-2-aminoformyl)ethyl)amino) methyl)-2-furyl)-4-quinazolinamine;
Number MS31:
N-(3-chloro-4-((3-fluorobenzyl)oxy)phenyl)-6-(5-(1-(2,3-dihydroxypropyl)amino)methyl-2-furyl)-4-quinazolinamine;
Number MS32:
N-(3-chloro-4-((3-fluorobenzyl)oxy)phenyl)-6-(5-((((4-carboxy-4-amino)butyl)amino)methyl)-2-furyl)-4-quinazolinamine;
Number MS33:
N-(3-chloro-4-((3-fluorobenzyl)oxy)phenyl)-6-(5-((morpholinyl)methyl)-2-thienyl)-4-quinazolinamine;
Number MS34:
N-(3-chloro-4-((3-fluorobenzyl)oxy)phenyl)-6-(5-((4-methylpiperazinyl)methyl)-2-pyrrolidinyl)-4-quinazolinamine;
Number MS35:
N-(3-chloro-4-((3-fluorobenzyl)oxy)phenyl)-6-(5-(((2-ethoxycarbonylethyl)amino)methyl)-2-furyl)-4-quinazolinamine.

Based on the compounds numbered MS1 to MS35, the above-described preferred technical solutions also include ten salt compounds as follows:

N-(3-chloro-4-((3-fluorobenzyl)oxy)phenyl)-6-(5-(((2-hydroxyethyl)amino)methyl)-2-furyl)-4-quinazolinamine.dimethylsulfonate;

N-(3-chloro-4-((3-fluorobenzyl)oxy)phenyl)-6-(5-((2-(1,3-dihydroxypropyl)amino)methyl)-2-furyl)-4-quinazolinamine.dimethylsulfonate;

N-(3-chloro-4-((3-fluorobenzyl)oxy)phenyl)-6-(5-(((2-ethoxycarbonylethyl)amino)methyl)-2-furyl)-4-quinazolinamine.dimethylsulfonate;

N-(3-chloro-4-((3-fluorobenzyl)oxy)phenyl)-6-(5-((bis(2-hydroxyethyl)amino)methyl)-2-furyl-4-quinazolinamine.dimethylsulfonate;

N-(3-chloro-4-((3-fluorobenzyl)oxy)phenyl)-6-(5-((4-hydroxybutyl)amino)methyl-2-furyl)-4-quinazolinamine.dimethylsulfonate;

N-(3-chloro-4-((3-fluorobenzyl)oxy)phenyl)-6-(5-(1-(2,3-dihydroxypropyl)amino)methyl-2-furyl)-4-quinazolinamine.dimethylsulfonate;

N-(3-chloro-4-((3-fluorobenzyl)oxy)phenyl)-6-(5-(((4-methoxybutyl)amino)methyl)-2-furyl)-4-quinazolinamine.dimethylsulfonate;

N-(3-chloro-4-((3-fluorobenzyl)oxy)phenyl)-6-(5-(((2-ethoxycarbonylethyl)amino)methyl)-2-furyl)-4-quinazolinamine.di-p-toluenesulfonate;

N-(3-chloro-4-((3-fluorobenzyl)oxy)phenyl)-6-(5-(((3-hydroxypropyl)amino)methyl)-2-furyl)-4-quinazolinamine.di-p-toluenesulfonate;

N-(3-chloro-4-((3-fluorobenzyl)oxy)phenyl)-6-(5-(((2-hydroxyethyl)amino)methyl)-2-furyl)-4-quinazolinamine.di-p-toluenesulfonate.

According to the present invention, the quinazoline derivatives of structural general formula (I) or pharmaceutically acceptable salts or solvates thereof are also selected from the compounds as shown in the following general formula:

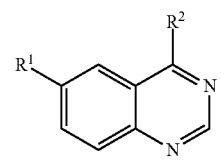

(I)

in this formula, $R^1$ is

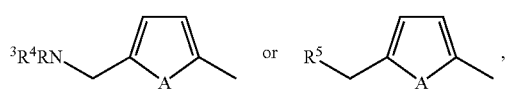

A is O, S, $NR^7$, wherein $R^7$ is H or $C_{1-6}$ alkyl;
$R^2$ is

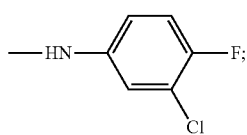

R³ and R⁴ are each independently selected from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

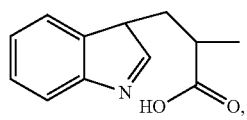

wherein said substituents are one or more groups selected from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkyl, optionally substituted heteroaryl $C_{1-6}$ alkyl, said substituent on the aryl or heteroaryl group is one or more group selected from hydroxy, mercapto, amino, nitro, halogen atoms, $C_{1-6}$ alkyl, $C_{1-6}$ alkoxy, $C_{1-6}$ alkylthio, carboxy;

R⁵ is a 3- to 8-membered heterocyclic group containing at least one heteroatom selected from N, O, S, which is optionally substituted by R⁶. Said R⁶ is selected from H or $C_{1-6}$ alkyl, halo-$C_{1-6}$ alkyl, and hydroxy-$C_{1-6}$ alkyl.

According to the preferred technical solutions of the present invention, in said general formula (I), R¹ is

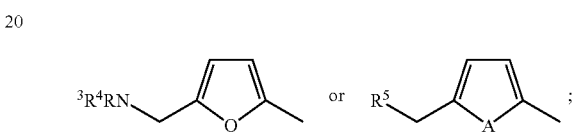

R² is

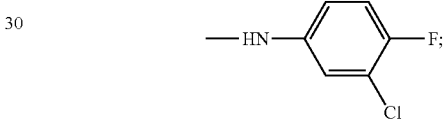

R³ and R⁴ are each independently selected from H, $C_{1-10}$ alkyl, $C_{2-10}$ alkenyl, $C_{3-10}$ cycloalkyl with substituents, $C_{3-10}$ alkenyl with substituents, $C_{1-10}$ alkyl with substituents, $C_{2-10}$ alkenyl with substituents or

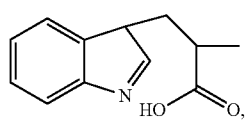

wherein said substituents are one or more groups selected from nitro, amino, carboxy, halogen, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryl oxy, optionally substituted aryl $C_{1-6}$ alkoxy, optionally substituted heteroaryl $C_{1-6}$ alkoxy, said substituent on the aryl or heteroaryl group is one or more group selected from hydroxy, mercapto, amino, nitro, halogen, $C_{1-6}$ alkyl, $C_{1-6}$ alkoxy, $C_{1-6}$ alkylthio, carboxy;

R⁵ is a 3- to 8-membered heterocyclic group containing at least one heteroatom selected from N, O, S, which is optionally substituted by R⁶. Said R⁶ is selected from H or $C_{1-6}$ alkyl, halo-$C_{1-6}$ alkyl, and hydroxy-$C_{1-6}$ alkyl.

According to the preferred technical solutions of the present invention, in the general formula (I), R¹ is

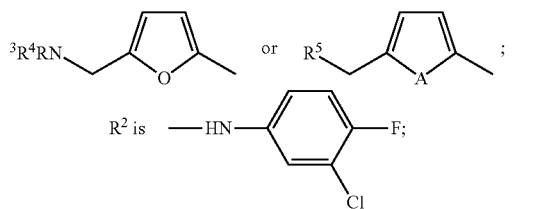

R² is

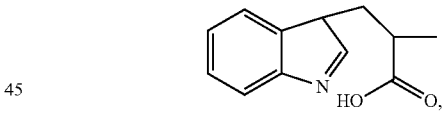

R³ is selected from $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

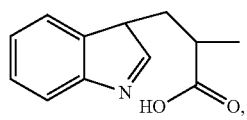

wherein said substituents are one or more groups selected from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted phenyl, optionally substituted benzyl, optionally substituted benzyloxy, said substituent on the benzene ring is one or more group selected from hydroxy, mercapto, amino, nitro, halogen, $C_{1-6}$ alkyl, $C_{1-6}$ alkoxy, $C_{1-6}$ alkylthio, carboxy;

R⁴ is H or $C_{1-6}$ alkyl;

R⁵ is a 3- to 8-membered heterocyclic group which contains at least one heteroatom selected from N, S, O and is connected to the methylene group via N atom. R⁵ is optionally substituted by R⁶, wherein said R⁶ is selected from H or $C_{1-6}$ alkyl, halo-$C_{1-6}$ alkyl and hydroxy-$C_{1-6}$ alkyl.

According to the preferred technical solutions of the present invention, in said general formula (I), $R^1$ is

[structure: furan with $R^4RN$-CH$_2$- substituent, or thiophene (A) with $R^5$-CH$_2$- substituent]

$R^2$ is

[structure: -HN-phenyl with F and Cl substituents]

$R^3$ is selected from $C_{2-10}$ alkenyl with substituents, $C_{1-10}$ alkyl with substituents, $C_{3-10}$ cycloalkyl with substituents, $C_{3-10}$ cycloalkenyl with substituents, or

[structure: indole-methyl connected to CH(CH$_3$)-C(=O)-OH]

wherein said substituents are one or more groups selected from nitro, amino, carboxy, halogen, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted phenyl, optionally substituted benzyl, optionally substituted benzyloxy, said substituent on the benzene ring is one or more group selected from hydroxy, mercapto, amino, nitro, halogen, $C_{1-6}$ alkyl, $C_{1-6}$ alkoxy, $C_{1-6}$ alkylthio, carboxy;

$R^4$ is H or $C_{1-4}$ alkyl;

$R^5$ is

[structure: 6-membered ring with Z and N, N attached by bond]

in which Z is S, O or $NR^6$, wherein said $R^6$ is selected from H or $C_{1-6}$ alkyl.

According to the preferred technical solutions of the present invention, said quinazoline derivatives or pharmaceutically acceptable salts or solvates thereof are selected from the following compounds numbered M36 to MS42:

Number MS36:
N-(3-chloro-4-fluorophenyl)-6-(5-(((propyl)amino)methyl)-2-furyl)-4-quinazolinamine;

Number MS37:
N-(3-chloro-4-fluorophenyl)-6-(5-((((4-carboxy-4-amino)butyl)amino)methyl)-2-furyl)-4-quinazolinamine;

Number MS38:
N-(3-chloro-4-fluorophenyl)-6-(5-((((1-carboxy-4-amino)butyl)amino)methyl)-2-furyl)-4-quinazolinamine;

Number MS39:
N-(3-chloro-4-fluorophenyl)-6-(5-(((2-butenyl)amino)methyl)-2-furyl)-4-quinazolinamine;

Number MS40:
N-(3-chloro-4-fluorophenyl)-6-(5-(((2-(4-nitrophenyl)ethyl)amino)methyl)-2-furyl)-4-quinazolinamine;

Number MS41:
N-(3-chloro-4-fluorophenyl)-6-(5-(((2-(cyclohexenyl)ethyl)amino)methyl)-2-furyl)-4-quinazolinamine Number MS42:
N-(3-chloro-4-((3-fluorobenzyl)oxy)phenyl)-6-(5-(((3-hydroxypropyl)amino)methyl)-2-furyl-4-quinazolinamine According to the present invention, said halogen or halogen atoms are selected from fluoro, chloro or bromo.

According to the present invention, said alkyl group is a linear or branched alkyl group, such as $C_{1-10}$ alkyl, preferably $C_{1-8}$ alkyl, more preferably $C_{1-6}$ alkyl, including but not limited to methyl, ethyl, propyl, isopropyl, butyl, isobutyl, tert-butyl, n-pentyl, isopentyl, neopentyl, n-hexyl.

According to the present invention, said alkenyl group is a linear or branched alkenyl group, such as $C_{2-10}$ alkenyl, preferably $C_{2-8}$ alkenyl, more preferably $C_{2-6}$ alkenyl, including but not limited to ethylenyl, propylenyl, butenyl, isobutenyl, pentenyl, isopentenyl, hexenyl.

According to the present invention, said alkynyl group is a linear or branched alkynyl group, such as $C_{2-10}$ alkynyl, preferably $C_{2-8}$ alkynyl, more preferably $C_{2-6}$ alkynyl, including but not limited to ethynyl, propynyl, butynyl.

According to the present invention, said cycloalkyl is a $C_{3-10}$ cycloalkyl group, preferably $C_{3-8}$ cycloalkyl group, more preferably $C_{3-6}$ cycloalkyl group, and more preferably cyclopropyl, cyclobutyl, cyclopentyl, cyclohexyl. Said cycloalkyl group is optionally substituted by the aforementioned substituents.

According to the present invention, said cycloalkenyl group is a $C_{3-10}$ cycloalkenyl group, preferably $C_{3-8}$ cycloalkenyl group, more preferably $C_{3-6}$ cycloalkenyl group, and more preferably cyclopropenyl, cyclobutenyl, cyclopentenyl, cyclohexenyl. Said cycloalkenyl group is optionally substituted by the aforementioned substituents.

According to the present invention, said heterocyclic group containing at least one, preferably 1-4 of N, O, S heteroatoms, is preferably 3-8-membered heterocyclic group, more preferably a 3-6 membered heterocyclic group e, such as tetrahydrofuran, tetrahydrothiophene, azetidine, acridine, pyrrolidine, 1,3-dihydro-thiazole, 1,3-dihydro-oxazole, piperidine, piperazine, morpholine, thiomorpholine, thiazine. Said heterocyclic group is optionally substituted by H or $C_{1-6}$ alkyl, preferably substituted by $C_{1-4}$ alkyl.

According to the present invention, said aryl group is a monocyclic or bicyclic aromatic hydrocarbon group, preferably phenyl, naphthyl, more preferably phenyl.

According to the present invention, the heteroaryl is a monocyclic or bicyclic hetero aromatic hydrocarbon group, in which the ring containing heteroatoms is preferably a 5- or 6-membered heteroaryl which contains at least one, preferably 1-4 of N, O, S heteroatoms. Said heteroaryl group is preferably pyridyl, pyrimidinyl, quinolyl, isoquinolyl, quinazolinyl, quinoxalinyl, indolyl, pyrrolyl, thienyl, furyl, benzofuryl, benzothienyl, thiazolyl, isothiazolyl, oxazolyl, isoxazolyl, pyrazolyl, furazanyl, thiadiazolyl, tetrazolyl, etc., and more preferably pyrrolyl, thienyl, furyl, indolyl, benzofuryl, and more preferably indolyl.

According to the present invention, the aryl groups of an aryl-$C_{1-6}$ alkyl group and aryloxy group are as defined above, and optionally substituted. The aryl-$C_{1-6}$ alkyl group is preferably a benzyl group.

According to the present invention, the heteroaryl groups of a heteroaryl-$C_{1-6}$ alkyl and heteroaryloxy group are as defined above, and optionally substituted by the above-described substituents. The heteroaryl $C_{1-6}$ alkyl group is preferably a pyridylmethyl group, thienylmethyl group, and furylmethyl group.

The term "pharmaceutically acceptable salts" in the present invention includes, but is not limited to salts formed with inorganic acids, such as hydrochloride, phosphate, diphosphate, hydrobromide, sulfate, sulfinate, nitrate and similar salts thereof; and also includes salts formed with organic acids, such as lactate, oxalate, malate, maleate, fumarate, tartrate, succinate, citrate, lactate, sulfonate, methanesulfonate, p-toluenesulfonate, 2-hydroxyethyl sulfonate, benzoate, salicylate, stearate, trifluoroacetate or amino acid salts and alkanoate such as acetate, HOOC—$(CH_2)_n$—COOH salts, where n is 0-4, and similar salts thereof. Similarly, pharmaceutically acceptable cations include, but are not limited to sodium, potassium, calcium, aluminum, lithium and ammonium.

The term solvate refers to a solvate formed from the quinazoline derivative of the general formula (I) or pharmaceutically acceptable salt thereof and a solvent. Said solvent is preferably water or a lower aliphatic alcohol, such as $C_{1-6}$ aliphatic alcohol. Said solvate is preferably hydrate or alcoholate.

The present invention also provides a preparation method of the quinazoline derivatives of the general formula (I) or pharmaceutically acceptable salts or solvates thereof

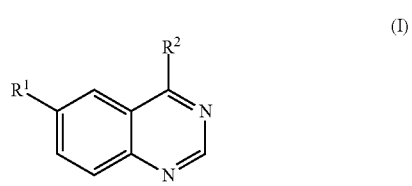

(I)

in the formula, $R^1$, $R^2$ are as defined above.

For example: $R^1$ is

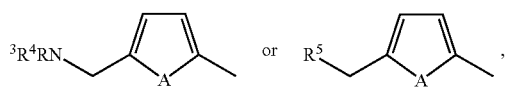

A is O, S, $NR^7$, wherein $R^7$ is H or $C_{1-6}$ alkyl;

$R^2$ is

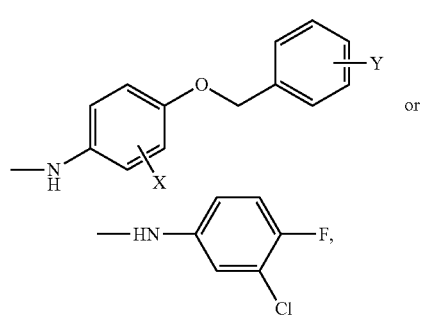

$R^3$ and $R^4$ are each independently selected from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

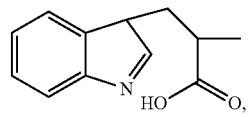

wherein said substituents are one or more groups selected from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, optionally substituted heteroaryl $C_{1-6}$ alkoxy, and said substituent on the aryl or heteroaryl group is one or more group selected from hydroxy, mercapto, amino, nitro, halogen, $C_{1-6}$ alkyl, $C_{1-6}$ alkoxy, $C_{1-6}$ alkylthio, carboxy;

$R^5$ is a 3- to 8-membered heterocyclic group containing at least one heteroatom selected from N, S, O, which is optionally substituted by $R^6$. Said $R^6$ is selected from H or $C_{1-6}$ alkyl, halo-$C_{1-6}$ alkyl, and hydroxy-$C_{1-6}$ alkyl.

Method 1: For the Following Formula (II)

formula (II)

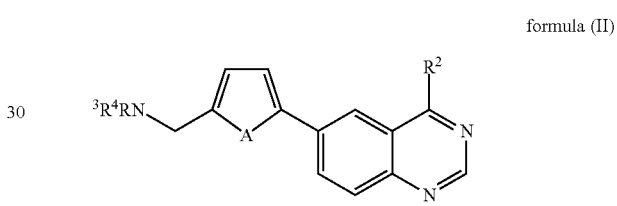

in which $R^2$, $R^3$, $R^4$ and A are as defined above;
said method comprises the preparation by acetalization of the compounds of formula (IV) and $HNR^3R^4$;

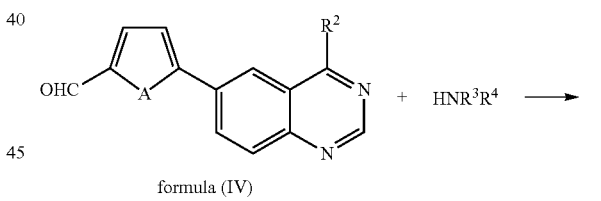

formula (IV)

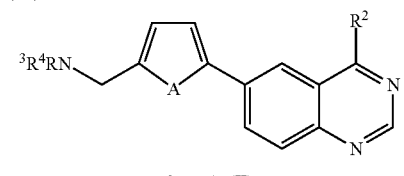

formula (II)

Method 2: For the Following Formula (III)

formula (III)

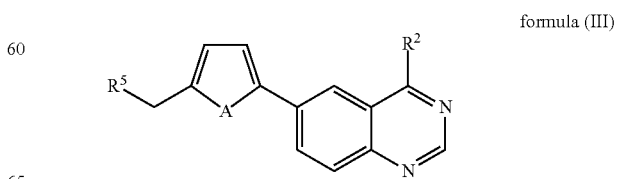

wherein $R^2$ and A are as defined above;

$R^5$ is a 3- to 8-membered heterocyclic group containing at least one heteroatom selected from N, S, O which is optionally substituted by $R^6$, wherein said $R^6$ is selected from H or $C_{1-6}$ alkyl, halo $C_{1-6}$ alkyl, hydroxy $C_{1-6}$ alkyl; said method comprises that the compounds of formula (V) and formula (VI) are subjected to acetalization, followed by removal of one molecule of water to give the corresponding imine, which is then subjected to reduction to give the target product of formula (III).

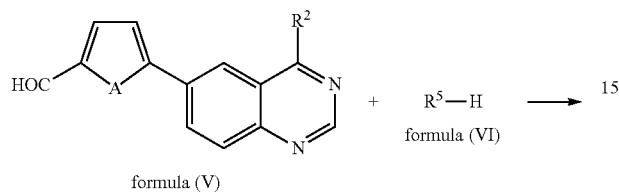

formula (V)    formula (VI)

formula (III)

Preferably, the preparation method of the prevent invention is as follows:

(1) for the quinazoline derivatives of structural general formula (II-1), which can be produced via the following reaction:

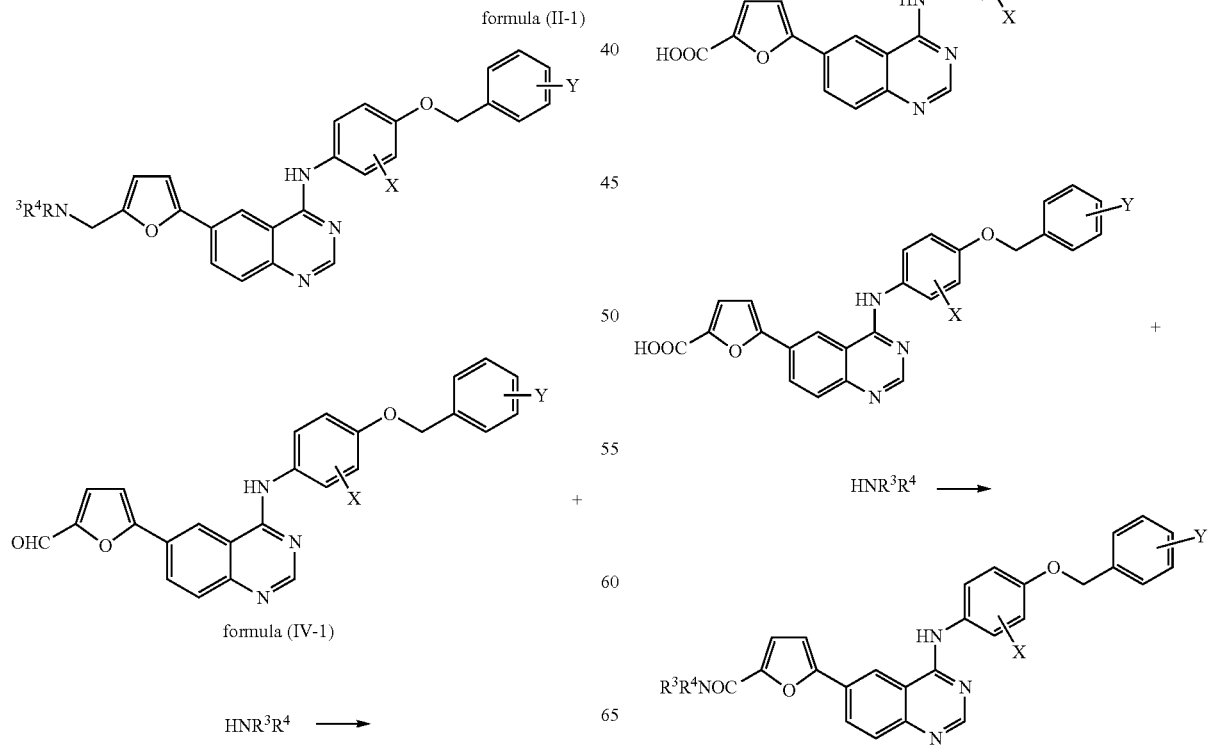

formula (II-1)

in which $R^3$, $R^4$, X and Y are as defined above.

The reaction principle is: the starting materials quinazoline furancarboxaldehyde and an amine are subjected to acetalization, followed by removal of one molecule of water to give the corresponding imine, which is then subjected to reduction to give the target product.

The compounds of formula (II-1) can also be prepared via the following steps:

-continued

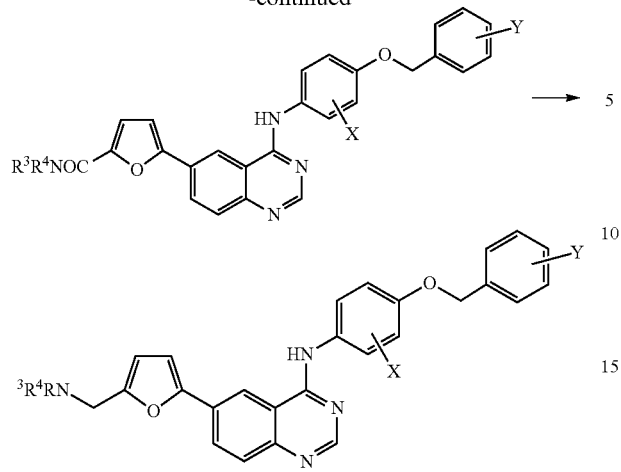

($R^3$, $R^4$, X and Y are as defined above.)

The reaction principle is: quinazolinyl furfural as a starting material is oxidized to give the corresponding furancarboxylc acid. Furancarboxylc acid reacted with an amine to obtain furanamide, which is then reduced to give a target product.

In the above-described reaction for synthesizing formula II-1, the starting material, quinazoine furfural is commercially available, but can also be produced. The production process is as follows: adding an appropriate amount of N-(3-chloro-4-(3-fluorobenzyloxy)phenyl)-6-iodo-4-quinazolinamine, 5-formylfuran-2-boric acid, 10% palladium on carbon (54% water content), 1,2-dimethoxyethane, methanol and triethylamine in a reaction flask. Heating and keeping at 50° C. and stirring for 24 h. The resulting reactant is hot filtered under suction and the mixture, and the filtrate is rotary evaporated. Methanol and water are added into the resulting residue, and stirred at 50° C. in a water bath. The mixture is filtered under suction, washed sequentially with water and methanol, and then dried under vacuum to give the product.

(2) for the quinazoline derivatives of structural general formula (II-2), which can be produced via the following reaction:

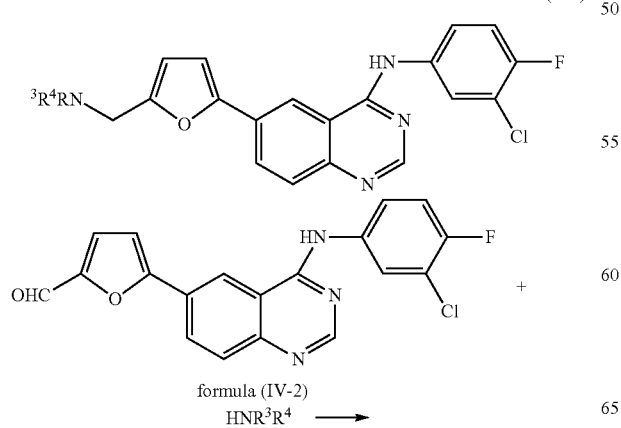

formula (IV-2)

HNR³R⁴ ⟶

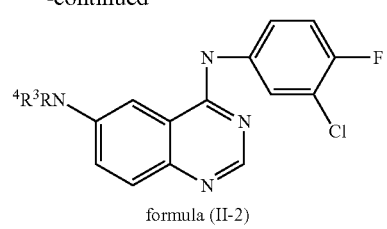

formula (II-2)

($R^3$ and $R^4$ are as defined above).

The reaction principle is: N-(3-chloro-4-fluorophenyl)-6-(5-formyl-2-furyl) 4-quinazolinamine (i.e. an intermediate of quinazoline derivatives) as a starting material is reacted with an amine via acetalization to give the target compound of formula (II-2), or said starting material is oxidized to give the corresponding furancarboxylc acid, which is then reacted with an amine to obtain furanamide. Furanamide is reduced to give the target product of formula (II-2).

(3) for the compounds of structural general formula (III), formula (III)

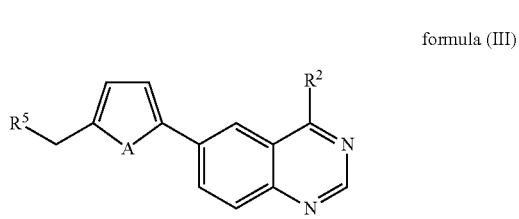

in which $R^2$ and A are defined the above-described;
$R^5$ is

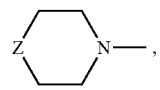

in which Z is S, O or $NR^6$, wherein said $R^6$ is selected from H or $C_{1-6}$ alkyl.

Said reaction includes acetalization of the compounds of formula (V) and formula (VI-1), removing one molecule of water to give the corresponding imine, which is then reduced to give the target product of formula (III-1).

-continued

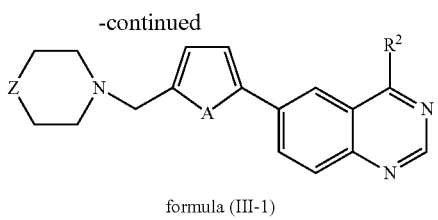

formula (III-1)

In the above-described reaction of formula III, the starting material, N-(3-chloro-4-fluorophenyl)-6-(5-formyl-2-furyl)-4-quinazolinamine is commercially available, but can also be produced. The preparation process is as follows: adding an appropriate amount of N-(3-chloro-4-fluorophenyl)-6-iodo-4-quinazolinamine, 5-formylfuran-2-boric acid, 10% palladium on carbon (54% water content), 1,2-dimethoxyethane, methanol and triethylamine in a reaction flask. Heating and keeping at 50° C. and stirring for 24 h. The resulting reactant is hot filtered under suction and the mixture, and the filtrate is rotary evaporated. Methanol and water are added into the resulting residue, and stirred at 50° C. in a water bath. The mixture is filtered under suction, washed sequentially with water and methanol, and then dried under vacuum to give the product.

The present invention also provides a pharmaceutical composition, comprising a pharmaceutically effective amount of the quinazoline derivatives of general formula (I) or pharmaceutically acceptable salts or solvates thereof, and pharmaceutically acceptable excipients or additives. The pharmaceutical compositions can be in the form of oral administration, for example tablets or capsules, and also in the form of sterile solutions, suspensions or emulsions for parenteral injection, such as intravenous, subcutaneous, intramuscular and intravascular injections.

The present invention also provides the use of the quinazoline derivatives of general formula (I) or pharmaceutically acceptable salts or solvates thereof in the preparation of anti-tumor or anti-cancer medicaments.

According to the present invention, said tumors or cancers are the cancers associated with the overexpression and/or overactivity of epidermal growth factor receptor family. The tumors or cancers are more preferably selected from bladder cancer, non-small cell lung cancer, ovarian cancer, breast cancer, stomach cancer, esophageal cancer, lung cancer, head and neck cancer, colon cancer, pharyngeal cancer and pancreatic cancer, and so on, particularly non-small cell lung cancer.

The present invention also provides the use of the quinazoline derivatives of general formula (I) or pharmaceutically acceptable salts or solvates thereof in the preparation of medicaments for diseases related to the overexpression and/or overactivity of epidermal growth factor receptor family, including EGFRI (epidermal growth factor receptor, EGFR), c-ErbB2/HER2 (generally HER2), c-ErbB3/HER3, c-ErbB4/HER4, and vascular epidermal growth factor (VEGFR). EGFR used herein, unless otherwise specified, means those receptors including wild-type and mutant receptors. The term "mutation" includes but is not limited to nucleotide deletion of a frame or substitution in one or more exons of encoding receptors such as EGFR.

Generally, the compounds of the present invention, particularly by inhibiting epidermal growth factor receptor tyrosine kinases, possess effective inhibitory activity against the erbB receptor tyrosine kinases family, while they also possess inhibitory activity against other tyrosine kinases. Relative to inhibiting VGFR tyrosine kinases, the compounds of the present invention have significantly more effective to inhibit tyrosine kinases of the EGFR family. It is indicated in the results of the protein tyrosine kinase inhibition test: 1) Most of the compounds provided in the present invention have better inhibition not only to EGFR1, EGFR2, $IC_{50}$<10 nM, but also to c-ErbB4/HER4, $IC_{50}$<25 nM; however, lapatinib has no effect on c-ErbB4/HER4; 2) Some compounds possess very good inhibitory activity against vascular epidermal growth factor receptor KDR; 3) In particular, the compounds of MS1, MS6, MS18, MS23, MS27, MS31, MS35, MS42, etc. and pharmaceutically acceptable dimethanesulfonate or di-p-toluenesulfonate thereof, possess better inhibitory activity against KDR; 4) Some compounds of the present invention still possess very good activity against tumor strains NC1-H1975, NC1-H460, etc., which have produced medicant resistant to lapatinib or in other words, produced mutant. The results of the test of human lung cancer A549 xenograft in nude mice further show that: the compounds provided in the present invention, particularly MS6, MS23, MS27, MS26, are better effective inhibition to human lung cancer A549 growth than the positive control lapatinib; 5) compounds MS33, MS34, compared with the similar structures in the prior art (for example, the four compounds explicitly excluded from the present invention), possess better inhibitory activity against EGFR, and also possess a very good inhibition to c-ErbB4/HER4.

In the present invention, by modification of quinazoline a series of novel structural compounds is obtained. By screening these compounds in respect of the activity of inhibiting tyrosine kinase, most of the compounds have been found to possess inhibitory activity against one or several tyrosine kinases in the epidermal growth factor receptor family, including EGFRI (epidermal growth factor receptor, EGFR), c-ErbB2/HER2 (generally HER2), c-ErbB3/HER3 and c-ErbB4/HER4, VEGFR-2, c-erbB-2, c-erbB-4, c-met, tie-2, PDGFR, c-src, lck, Zap70, fyn. Some compounds are selected for in vivo anti-tumor activity screening. The compounds have been found to have remarkable anti-tumor activity, very low toxicity in the tested animals. Such effect is surprising.

The present invention has the advantages of reasonable design, broad source of and easy access to the raw materials, simple and easy operation of the preparation methods, mild reaction conditions, high yield of the products and being beneficial for industrial-scale production.

Specific Mode for Carrying Out the Invention

Hereinafter, the present invention will be further illustrated with reference to the specific examples. But the protected scope of the present invention is not limited to the range disclosed in the following examples. It should be noted that the following examples do not constitue a limitation of the protection scope of the present invention. Any modification based on the present invention would not depart from the spirits of the present invention.

Example 1

Preparation of N-(3-chloro-4-((3-fluorobenzyl)oxy) phenyl)-6-(5-formyl-2-furyl)-4-quinazolinamine To a reaction flask N-(3-chloro-4-(3-fluorobenzyloxy) phenyl)-6-iodo-4-quinazolinamine (25.29 g, 50 mmol), 5-formylfuran-2-boric acid (10.50 g, 75 mmol), 10% palladium on carbon (1.25 g, 54% water content), 1,2-dimethoxyethane (400 ml), methanol (200 ml) and triethylamine (21 ml, 150 mmol) were added. The mixture was heated to and kept at 50° C. and stirring for 24 h. The resulting reactant is hot filtered under suction and the mixture, and the filtrate is rotary evaporated. Methanol (150 ml) and water (50 ml) were added in the obtained residue. The mixture was stirred at 50° C. in a water bath and then filtered under suction, washed sequentially with water and methanol, and dried under vacuum to afford a orange solid (22.6 g, 95.5%), i.e. the target product. m.p.: 225.5-228.4° C.; $^1$H NMR (DMSO-$d_6$) δ: 10.04 (s, 1H), 9.64 (s, 1H), 8.98 (s, 1H), 8.56 (s, 1H), 8.23 (d, J=9.0 Hz, 1H), 7.97 (d, J=2.5 Hz, 1H), 7.80 (d, J=8.0 Hz, 1H), 7.68-7.72 (m, 2H), 7.43-7.48 (m, 1H), 7.35 (d, J=9.0 Hz, 1H), 7.24-7.33 (m, 3H), 7.17 (m, 1H), 5.23 (s, 2H); ESI-MS m/z: 474[M+H]$^+$.

Example 2

Preparation of N-(3-chloro-4-((3-fluorobenzyl)oxy) phenyl)-6-(5-(((4-hydroxybutyl)amino)methyl)-2-furyl)-4-quinazolinamine (MS1)

In the present invention, the compound of Number MS1 can be synthesized via the following reaction route:

(step 1)

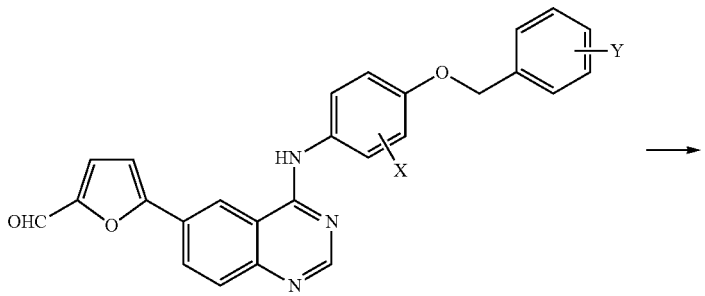

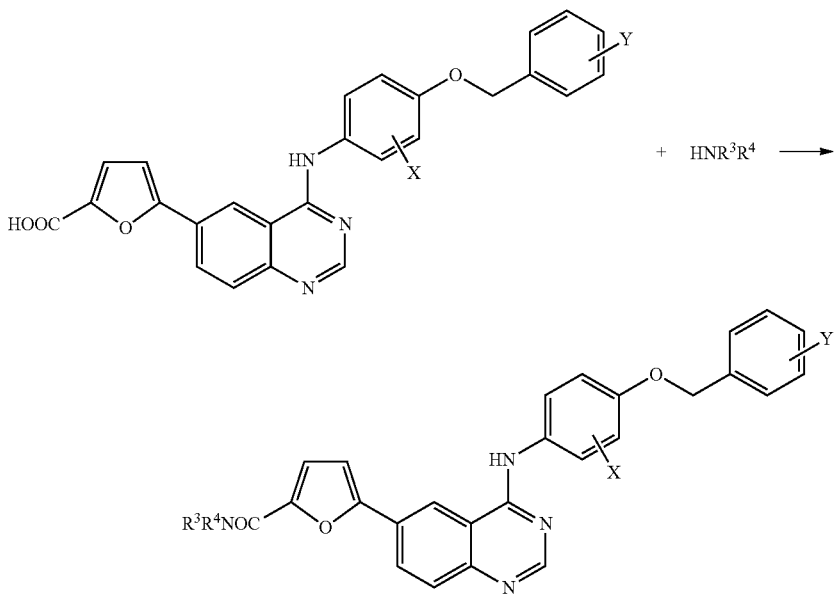

1p;2p
(step 2)

(step 3)

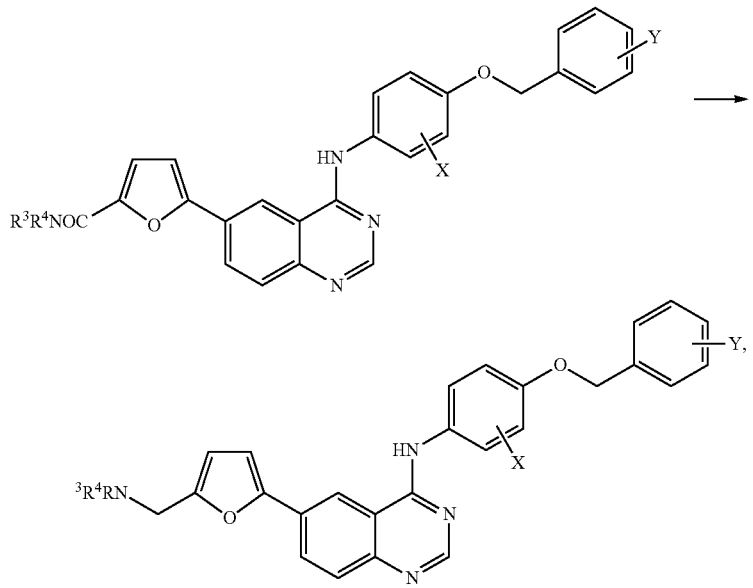

in which X is chloro, Y is fluoro, and the specific production steps are as follows:

Step 1: Preparation of N-(3-chloro-4-((3-fluorobenzyl)oxy)phenyl)-6-(5-carboxy-2-furyl)-4-quinazolinamine (Intermediate a)

N-(3-chloro-4-((3-fluorobenzyl)oxy)phenyl)-6-(5-formyl-2-furyl)-4-quinazolinamine (4.71 g) produced in Example 1 was added THF (60 ml), tetrabutylammonium bromide (0.1 g). Then a solution of potassium permanganate dissolved in water (70 ml) was slowly added dropwise to the mixture under ice-water cooling. After the addition was complete, the resulting brown suspension was reacted at room temperature for 24 h. The mixture was filtered under suction and the filter cake was washed with warm water of 40° C. three times, and methanol three times, and was refined to obtain an intermediate product a, 4.0 g;

Step 2: Preparation of N-(3-chloro-4-((3-fluorobenzyl)oxy)phenyl)-6-(5-(((4-hydroxybutyl)amino)formyl)-2-furyl)-4-quinazolinamine (Intermediate b)

To the intermediate a (0.98 g, 1 mmol) obtained from the above step 1 was added chloroform (50 ml), a drop of DMF. Thionyl chloride (0.3 ml) was then added at room temperature. After the mixture was reacted for 6 h, 4-hydroxybutylamine (4 ml) was added. The reaction was kept at room temperature for 24 h. After treatment the intermediate product b was obtained, 0.70 g;

Step 3: Preparation of N-(3-chloro-4-((3-fluorobenzyl)oxy)phenyl)-6-(5-(((4-hydroxybutyl)amino)methyl)-2-furyl)-4-quinazolinamine (Target Product MS1)

The intermediate b obtained from the above step 2 was reduced. After reaction the target product of compound MS 1 was obtained. The characterization of the related structures can be found in Example 3.

In the present invention, the compounds of Number MS1 to MS30 or di-p-toluenesulfonate thereof can also be synthesized via the following reaction route:

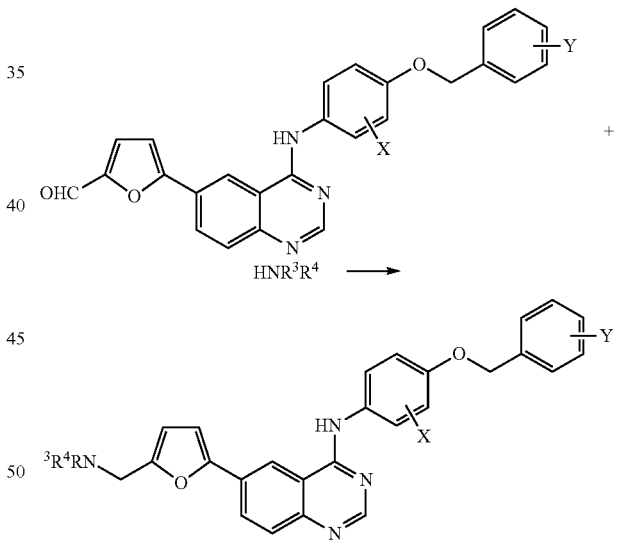

(in which X is chloro, Y is fluoro), the preparation process of each compound of MS1 to MS30 or salts thereof would be described in detail in Example 3 to Example 33.

Example 3

Preparation of N-(3-chloro-4-((3-fluorobenzyl)oxy)phenyl)-6-(5-(((4-hydroxybutyl)amino)methyl)-2-furyl)-4-quinazolinamine)(MS1).dimethylsulfonate N-(3-chloro-4-((3-fluorobenzyl)oxy)phenyl)-6-(5-formyl-2-furyl)-4-quinazolinamine (5.69 g, 12 mmol) obtained from Example 1 was dissolved in tetrahydrofuran (100 ml), and 4-hydroxy-1-butylamine (2.22 g, 25 mmol) was added. The mixture was stirred under nitrogen at room temperature for 6 h. Sodium triacetoxy borohydride (8.48 g, 40 mmol) was added, and then the mixture was stirred at room temperature for 12 h. To the mixture was added saturated aqueous solution of sodium carbonate (50 ml), and the mixture was stirred for 15 min and then layered. The organic layer was washed with saturated aqueous solution of sodium chloride, dried over anhydrous sodium sulfate, filtered, and rotary evaporated to give a yellow powdered solid, i.e. the compound of Number MS1. The yellow powdered solid was dissolved in tetrahydrofuran (50 ml), and then a solution of methanesulfonic acid (3.46 g, 36 mmol) in tetrahydrofuran (50 ml) was added dropwise under stirring. After addition, the mixture was stirred at room temperature for 12 h. The mixture was filtered under suction and the filter cake was washed with tetrahydrofuran-deionized water (95:5). The product was refined, and dried at 70° C. under vacuum to afford a yellow solid (7.51 g, 88.0%), i.e. the dimethanesolfonate of the compound of Number MS1. m.p.: 257.9-260° C.; 1H NMR (DMSO-$d_6$) $^1$H NMR (DMSO-$d_6$) δ: 8.49 (s, 1H), 8.22 (1H), 8.06 (1H), 8.05 (1H), 7.43 (1H), 7.36 (1H), 7.24 (d, 1H), 7.17 (1H), 6.90 (m, 1H), 6.7 (2H), 6.28 (1H), 5.16 (2H), 4.0 (1H), 3.66 (2H), 3.65 (1H), 3.50 (2H), 3.29 (6H), 2.55 (2H), 2.0 (3H), 1.53 (2H), 1.38 (2H); ESI-MS m/z: 547[M+H]$^+$.

N-(3-chloro-4-((3-fluorobenzyl)oxy)phenyl)-6-(5-((3-phenylpropyl)amino)methyl)-2-furyl)-4-quinazolinamine can be prepared by the same method, m.p.: 156-160° C.;

Example 4

Preparation of N-(3-chloro-4-((3-fluorobenzyl)oxy) phenyl)-6-(5-((n-hexylamino)methyl)-2-furyl)-4-quinazolinamine (MS2)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of hexylamine (0.20 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with A saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.43 g, 76.9%), i.e. the compound of Number MS2. $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 2.56 (t, 2H), 1.38 (s, 2H), 1.29-1.31 (m, 6H), 1.01 (t, 3H); ESI-MS m/z: 559[M+H]$^+$.

Example 5

Preparation of N-(3-chloro-4-((3-fluorobenzyl)oxy) phenyl)-6-(5-((ethylamino)methyl)-2-furyl)-4-quinazolinamine (MS3)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of ethylamine (0.09 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.40 g, 79.5%), i.e. the compound of Number MS3. 1H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 2.59 (m, 2H), 1.02 (t, 3H); ESI-MS m/z: 503 [M+H]+.

Example 6

Preparation of N-(3-chloro-4-((3-fluorobenzyl)oxy) phenyl)-6-(5-((N,N-diethyl)amino)methyl)-2-furyl)-4-quinazolinamine (MS4)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of N,N-diethylamine (0.15 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.38 g, 73.5%), i.e. the compound of Number MS4. $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 4H), 3.76 (s, 2H), 2.64 (m, 2H), 2.26 (s, 3H), 1.02 (t, 3H); ESI-MS m/z: 531[M+H]$^+$.

Example 7

Preparation of N-(3-chloro-4-((3-fluorobenzyl)oxy) phenyl)-6-(5-(((2-butenyl)amino)methyl)-2-furyl)-4-quinazolinamine (MS5)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 2-butenylamine (0.18 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.42 g, 77.1%), i.e. the compound of Number MS5. $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.76 (s, 2H), 2.55 (t, 1H), 1.62 (m, 1H), 1.39 (m, 1H), 0.98 (d, 6H); ESI-MS m/z: 543[M+H]$^+$.

Example 8

Preparation of N-(3-chloro-4-((3-fluorobenzyl)oxy) phenyl)-6-((5-(2-(1,3-dihydroxypropyl)amino) methyl)-2-furyl)-4-quinazolinamine (MS6).dimethylsulfonate N-(3-chloro-4-((3-fluorobenzyl)oxy)phenyl)-6-(5-formyl-2-furyl)-4-quinazolinamine (5.69 g, 12 mmol) obtained from Example 1 was dissolved in tetrahydrofuran (100 ml), followed by the addition of 2-amino-1,3-propanediol (2.28 g, 25 mmol). The mixture was stirred under nitrogen at room temperature for 6 h, followed by the addition of sodium triacetoxy borohydride (8.48 g, 40 mmol), and then stirred at room temperature for 12 h. A saturated aqueous solution of sodium carbonate (50 ml) was added, and then the mixture was stirred for 15 min to be layered. The organic layer was washed with saturated aqueous solution of sodium chloride, dried over anhydrous sodium sulfate, filtered, and rotary evaporated to give a yellow powdered solid, i.e. the compound of Number MS6. The yellow powdered solid was dissolved in tetrahydrofuran (50 ml), and a solution of methanesulfonic acid (3.46 g, 36 mmol) in tetrahydrofuran (50 ml) was added under stirring. After addition, the mixture was stirred at room temperature for 12 h. The mixture was filtered under suction and the filter cake was washed with tetrahydrofuran-deionized water (95: 5). The product was refined, and dried at 70° C. under vacuum to give a yellow solid (7.71 g, 86.7%), i.e. the dimethanesolfonate of the compound of Number MS6. HPLC: >98.5%, m.p.: 234-236° C.; $^1$H NMR (DMSO-$d_6$) δ: $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.277.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 3.66 (br, 2H), 3.60 (m, 4H), 2.73 (m, 1H); ESI-MS m/z: 549[M+H]+.

Example 9

Preparation of N-(3-chloro-4-((3-fluorobenzyl)oxy) phenyl)-6-((5-(((cyclohexylmethyl)amino)methyl)-2-furyl)-4-quinazolinamine (MS7)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of cyclohexyl-methylamine (0.23 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.42 g, 73.5%), i.e. the compound of Number MS7. $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-47.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 2.51 (d, 2H), 1.49-1.67 (m, 11H); ESI-MS m/z: 571[M+H]$^+$.

Example 10

Preparation of N-(3-chloro-4-((3-fluorobenzyl)oxy) phenyl)-6-(5-(((2-(3-cyclohexenyl)ethyl)amino) methyl)-2-furyl)-4-quinazolinamine (MS8)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 2-(1-cyclohexenyl)ethylamine (0.23 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.40 g, 68.8%), i.e. the compound of Number MS8. m.p.: 90-92° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.37 (t, 1H), 5.26 (s, 2H), 3.99-4.04 (m, 1H), 3.66 (s, 2H), 2.59 (t, 2H), 2.08 (t, 2H), 1.96 (t, 4H), 1.74 (m, 4H); ESI-MS m/z: 583[M+H]$^+$.

Example 11

Preparation of N-(3-chloro-4-((3-fluorobenzyl)oxy) phenyl)-6-(5-((((3-chlorocyclohexyl)methyl)amino) methyl)-2-furyl)-4-quinazolinamine (MS9)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 3-chlorocyclohexyl-methylamine (0.30 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.37 g, 61.1%), i.e. the compound of Number MS9. m.p.: 93-96° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 3.46 (s, 1H), 2.66 (d, 2H), 1.49-1.76 (m, 9H); ESI-MS m/z: 605[M+H]$^+$.

Example 12

Preparation of N-(3-chloro-4-((3-fluorobenzyl)oxy)phenyl)-6-(5-(((4-methoxybutyl)amino)methyl)-2-furyl)-4-quinazolinamine (MS10).dimethylsulfonate Under nitrogen, the compound of Number MS1, i.e. N-(3-chloro-4-((3-fluorobenzyl)oxy)phenyl)-6-(5-(((4-hydroxybutyl)amino)methyl)-2-furyl)-4-quinazolinamine.dimethanesulfonate (1.73 g, 2.3 mmol) prepared from Example 2 or Example 3, was dissolved in methanol (20 ml), followed by the addition of concentrated sulfuric acid (1.0 ml), and stirred under reflux for 12 h. The mixture was cooled down under stirring to precipitate a yellow solid. The mixture was filtered under suction, and the filter cake washed with anhydrous methanol, alkalized in ethanol. Salts were formed with methanesulfonic acid, and refined to give the dimethanesulfonate of the compound of Number MS10 (1.3 g). HPLC: >97.5%. $^1$H NMR (DMSO-d$_6$): 8.49 (s, 1H), 8.22 (1H), 8.06 (1H), 8.05 (1H), 7.43 (1H), 7.36 (1H), 7.24 (d, 1H), 7.17 (1H), 7.01 (1H), 6.90 (m, 1H), 6.7 (1H), 6.68 (1H), 6.26 (1H), 5.16 (2H), 4.0 (1H), 3.81 (2H), 3.66 (2H), 3.65 (1H), 3.58 (1H), 3.54 (1H), 3.29 (6H), 2.83 (2H), 2.0 (3H); ESI-MS m/z: 562[M+H]$^+$.

Example 13

Preparation of N-(3-chloro-4-((3-fluorobenzyl)oxy)phenyl)-6-(5-(((3-chlorobenzyl)amino)methyl)-2-furyl)-4-quinazolinamine (MS11)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 3-chlorobenzylamine (0.28 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.38 g, 63.3%), i.e. the compound of Number MS11. m.p.: 103-105° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 5H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.76-3.66 (s, 4H); ESI-MS m/z: 599[M+H]$^+$.

Example 14

Preparation of N-(3-chloro-4-((3-fluorobenzyl)oxy)phenyl)-6-(5-(((2-(4-nitrophenyl)ethyl)amino)methyl)-2-furyl)-4-quinazolinamine (MS12)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of 2-(4-nitrophenyl)ethylamine hydrochloride (0.41 g, 2 mmol) and diisopropylethylamine (0.26 g, 2 mmol), and stirred at room temperature for 6 h. Sodium triacetoxy borohydride (0.74 g, 3.5 mmol) was added, and the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow powdered solid (0.31 g, 49.7%), i.e. the compound of Number MS12. m.p.: 112-114° C.; $^1$H NMR (DMSO-d$_6$) δ: 9.87 (s, 1H), 8.74 (s, 1H), 8.56 (s, 1H), 8.21 (s, 2H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 3H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 2.84 (t, 2H), 2.69 (t, 2H); ESI-MS m/z: 624[M+H]$^+$.

Example 15

Preparation of N-(3-chloro-4-((3-fluorobenzyl)oxy)phenyl)-6-(5-(((2-(4-hydroxyphenyl)ethyl)amino)methyl)-2-furyl)-4-quinazolinamine (MS13)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of p-hydroxy-phenylethylamine (0.28 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.41 g, 68.9%), i.e. the compound of Number MS13. m.p.: 125-127° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.12-7.18 (m, 3H), 7.05 (d, J=3.2 Hz, 1H), 6.70 (d, 2H), 6.49 (d, J=3.3 Hz, 1H), 5.35 (s, 1H), 5.26 (s, 2H), 3.99-4.04 (m, 1H), 3.66 (s, 2H), 2.84 (t, 2H), 2.69 (t, 2H); ESI-MS m/z: 595[M+H]$^+$.

Example 16

Preparation of N-(3-chloro-4-((3-fluorobenzyl)oxy)phenyl)-6-(5-(((2-(3,5-dimethoxyphenyl)ethylamino)methyl)-2-furyl)-4-quinazolinamine (MS14)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 3,5-dimethoxy-phenylethylamine (0.36 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.45 g, 70.4%), i.e. the compound of Number MS14. m.p.: 101-104° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.63 (s, 2H), 6.49 (d, J=3.3 Hz, 1H), 6.19 (s, 1H), 5.26 (s, 2H), 3.99-4.04 (m, 1H), 3.82 (s, 6H), 3.66 (s, 2H), 2.84 (t, 2H), 2.69 (t, 2H); ESI-MS m/z: 639[M+H]$^+$.

Example 17

Preparation of N-(3-chloro-4-((3-fluorobenzyl)oxy) phenyl)-6-(5-(((2-(3-hydroxy-5-fluorophenyl)ethyl) amino)methyl)-2-furyl)-4-quinazolinamine (MS15)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 2-(3-fluoro-5-hydroxyphenyl)ethylamine (0.31 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.35 g, 57.1%), i.e. the compound of Number MS15. m.p.: 116-119° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.92 (s, 1H), 6.80 (s, 1H), 6.49 (d, J=3.3 Hz, 1H), 6.39 (s, 1H), 5.35 (s, 1H), 5.26 (s, 2H), 3.99-4.04 (m, 1H), 3.84 (s, 2H), 2.84 (t, 2H), 2.69 (t, 2H); ESI-MS m/z: 613[M+H]$^+$.

Example 18

Preparation of N-(3-chloro-4-((3-fluorobenzyl)oxy) phenyl)-6-(5-(((2-(3-chloro-5-fluorophenyl)ethyl) amino)methyl)-2-furyl)-4-quinazolinamine (MS16)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 2-(3-chloro-5-fluorophenyl)ethylamine (0.35 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.42 g, 66.6%), i.e. the compound of Number MS16. m.p.: 105-107° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.63 (s, 2H), 6.49 (d, J=3.3 Hz, 1H), 6.19 (s, 1H), 5.26 (s, 2H), 3.99-4.04 (m, 1H), 3.66 (s, 2H), 2.84 (t, 2H), 2.69 (t, 2H); ESI-MS m/z: 631[M+H]$^+$.

Example 19

Preparation of N-(3-chloro-4-((3-fluorobenzyl)oxy) phenyl)-6-(5-(((2,6-dihydroxyhexyl)amino)methyl)-2-furyl)-4-quinazolinamine (MS17)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of (±)-6-amino-1,5-hexanediol (0.27 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.40 g, 67.6%), i.e. the compound of Number MS17. m.p.: 123-125° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.277.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 3.65 (br, 2H), 3.54-3.58 (m, 3H), 2.83 (d, 2H), 1.44-1.48 (m, 4H), 1.25 (m, 2H); ESI-MS m/z: 591[M+H]$^+$.

Example 20

Preparation of N-(3-chloro-4-((3-fluorobenzyl)oxy) phenyl)-6-(5-((bis(2-hydroxyethyl)amino)methyl)-2-furyl)-4-quinazolinamine (MS 18).dimethylsulfonate Under nitrogen, N-(3-chloro-4-((3-fluorobenzyl)oxy)phenyl)-6-(5-formyl-2-furyl)-4-quinazolinamine (5.69 g, 12 mmol) obtained from Example 1 was dissolved in tetrahydrofuran (100 ml), followed by the addition of diethanolamine (1.53 g, 25 mmol), and stirred at room temperature for 6 h. Sodium triacetoxy borohydride (8.48 g, 40 mmol) was slowly added in batches, and then the mixture was stirred at room temperature for 12 h. A saturated aqueous solution of sodium carbonate (50 ml) was added, and the mixture was stirred for 15 min to be layered. The organic layer was washed with saturated aqueous solution of sodium chloride, dried over anhydrous sodium sulfate, filtered, and rotary evaporated to give a yellow powdered solid. The yellow powdered solid was dissolved in tetrahydrofuran (50 ml), and a solution of methanesulfonic acid (3.46 g, 36 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid 6.71 g, i.e. the dimethanesulfonate of the compound of Number MS18. HPLC: >98.5%. 1H NMR (DMSO-$d_6$) δ: 8.49 (s, 1H), 8.22 (1H), 8.06 (2H), 7.36 (2H), 7.17 (2H), 7.01 (1H), 6.09 (1H), 6.7 (2H), 6.28 (1H), 6.68 (1H), 6.26 (1H), 5.16 (2H), 4.0 (1H), 3.76 (2H), 3.65 (2H), 3.45 (4H), 3.29 (6H), 2.53 (3H), 2.21 (3H), 2.0 (2H) ESI-MS m/z: 563[M+H]$^+$.

Example 21

Preparation of N-(3-chloro-4-((3-fluorobenzyl)oxy)phenyl)-6-(5-(((benzyloxy)amino)methyl)-2-furyl)-4-quinazolinamine (MS19)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of O-benzylhydroxyamine hydrochloride (0.34 g, 2 mmol) and diisopropylethylamine (0.26 g, 2 mmol), and stirred at room temperature for 6 h. Sodium triacetoxy borohydride (0.74 g, 3.5 mmol) was added, and the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.31 g, 53.3%), i.e. the compound of Number MS19. m.p.: 117-119° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 3H), 7.27-7.38 (m, 6H), 7.18 (t, 1H), 7.05 (d, J=3.2 Hz, 1H), 6.49 (d, J=3.3 Hz, 1H), 5.26 (s, 2H), 4.79 (s, 2H), 3.99-4.04 (m, 1H), 3.76 (s, 2H); ESI-MS m/z: 581[M+H]$^+$.

Example 22

Preparation of N-(3-chloro-4-((3-fluorobenzyl)oxy)phenyl)-6-(5-(((2-(3-chlorophenyl)ethyl)amino)methyl)-2-furyl)-4-quinazolinamine (MS20)

The preparation method of the Example is the same as in Example 17, using 2-(3-chlorophenyl)ethylamine as starting material, TLC tracking to the end of the reaction. Under nitrogen, a yellow solid, i.e. the compound of Number MS20 was obtained. m.p.: 104-106° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 5H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 2.69 (m, 4H); ESI-MS m/z: 613[M+H]$^+$.

Example 23

Preparation of N-(3-chloro-4-((3-fluorobenzyl)oxy)phenyl)-6-(5-(((3-aminocyclohexyl)amino)methyl)-2-furyl)-4-quinazolinamine (MS21)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of 1,3-diaminocyclohexane (0.23 g, 2 mmol), and stirred at room temperature for 6 h. Sodium triacetoxy borohydride (0.42 g, 2 mmol) was added, and then the mixture was stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a nearly yellow solid. The solid was separated by column chromatography on silica gel (200-300 mesh) (eluted with a gradient of ethyl acetate/methanol) to give a yellow solid (0.33 g, 57.7%), i.e. the compound of Number MS21. m.p.: 122-125° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 5.11 (d, 2H), 3.99-4.04 (m, 1H), 3.84 (s, 2H), 2.80 (m, 2H), 1.21-1.49 (m, 8H); ESI-MS m/z: 572[M+H]$^+$.

Example 24

Preparation of N-(3-chloro-4-((3-fluorobenzyl)oxy)phenyl)-6-(5-(((carboxymethyl)amino)methyl)-2-furyl)-4-quinazolinamine (MS22)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of glycine methyl ester hydrochloride (0.22 g, 2 mmol), added diisopropylethylamine (0.26 g, 2 mmol), and stirred at room temperature for 6 h. Sodium triacetoxy borohydride (0.74 g, 3.5 mmol) was added, and then stirred at room temperature for 24 h. 20% aqueous solution of sodium hydroxide (10 ml) was added and the mixture was stirred for 2 h, and then adjusted to PH~7 with hydrochloric acid. The organic layer was washed with saturated aqueous solution of sodium chloride, dried over anhydrous sodium sulfate, filtered, and rotary evaporated to give a brownish yellow solid (0.36 g, 67.5%), i.e. the compound of Number MS22. m.p.: 136-139° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 3.49 (s, 2H); ESI-MS m/z: 533[M+H]$^+$.

The following compounds can be prepared by the same method:

N-(3-chloro-4-((3-fluorobenzyl)oxy)phenyl)-6-(5-(((1-carboxyethyl)amino)methyl)-2-furyl)-4-quinazolinamine; m.p.: 139-141° C.

N-(3-chloro-4-((3-fluorobenzyl)oxy)phenyl)-6-(5-(((1-carboxybutyl)amino)methyl)-2-furyl)-4-quinazolinamine, m.p.: 131-135° C.

N-(3-chloro-4-((3-fluorobenzyl)oxy)phenyl)-6-(5-(((1-carboxy-3-methylbutyl)amino)methyl)-2-furyl)-4-quinazolinamine, m.p.: 128-130° C.

N-(3-chloro-4-((3-fluorobenzyl)oxy)phenyl)-6-(5-(((1-carboxy-2-methylpropyl)amino)methyl)-2-furyl)-4-quinazolinamine, m.p.: 146-150° C.

N-(3-chloro-4-((3-fluorobenzyl)oxy)phenyl)-6-(5-(((1-carboxy-2-methylbutyl)amino)methyl)-2-furyl)-4-quinazolinamine, m.p.: 133-137° C.

N-(3-chloro-4-((3-fluorobenzyl)oxy)phenyl)-6-(5-(((1-carboxy-4-amino-4-oxobutyl)amino)methyl)-2-furyl)-4-quinazolinamine, m.p.: 160-165° C.

N-(3-chloro-4-((3-fluorobenzyl)oxy)phenyl)-6-(5-(((1-carboxy-2-hydroxypropyl)amino)methyl)-2-furyl)-4-quinazolinamine, m.p.: 184-187° C.

N-(3-chloro-4-((3-fluorobenzyl)oxy)phenyl)-6-(5-(((1-carboxy-3-(3H-indol-3-yl)propyl)amino)methyl)-2-furyl)-4-quinazolinamine, m.p.: 123-126° C.

Example 25

Preparation of N-(3-chloro-4-((3-fluorobenzyl)oxy) phenyl)-6-(5-(((1,3-dicarboxypropyl)amino)methyl)-2-furyl)-4-quinazolinamine (MS23)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of glutamic acid dimethyl ester hydrochloride (0.42 g, 2 mmol) and diisopropylethylamine (0.26 g, 2 mmol), and stirred at room temperature for 6 h. Sodium triacetoxy borohydride (0.74 g, 3.5 mmol) was added, and then the mixture was stirred at room temperature for 48 h. 20% aqueous solution of sodium hydroxide (10 ml) was added and the mixture was stirred for 2 h, and then adjusted to PH~7 with hydrochloric acid. The organic layer was washed with saturated aqueous solution of sodium chloride, dried over anhydrous sodium sulfate, filtered, and rotary evaporated to give a yellow solid (0.37 g, 61.2%), i.e. the compound of Number MS23. m.p.: 158-160° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 3.49 (t, 1H), 2.33 (t, 2H), 1.91 (m, 2H); ESI-MS m/z: 605[M+H]$^+$.

Example 26

Preparation of N-(3-chloro-4-((3-fluorobenzyl)oxy) phenyl)-6-(5-((((1-carboxy-2-phenyl)ethyl)amino) methyl)-2-furyl)-4-quinazolinamine (MS24)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of phenylalanine methyl ester hydrochloride (0.43 g, 2 mmol) and diisopropylethylamine (0.26 g, 2 mmol), and stirred at room temperature for 6 h. Sodium triacetoxy borohydride (0.74 g, 3.5 mmol) was added, and then the mixture was stirred at room temperature for 48 h. 20% aqueous solution of sodium hydroxide (10 ml) was added and the mixture was stirred for 2 h, and then adjusted to PH~7 with hydrochloric acid. The organic layer was washed with saturated aqueous solution of sodium chloride, dried over anhydrous sodium sulfate, filtered, and rotary evaporated to give a yellow solid (0.33 g, 53.0%), i.e. the compound of Number MS24. m.p.: 139-141° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 3H), 7.27-7.35 (m, 6H), 7.18 (t, 1H), 7.05 (d, J=3.2 Hz, 1H), 6.49 (d, J=3.3 Hz, 1H), 5.26 (s, 2H), 3.99-4.04 (m, 1H), 3.88 (t, 1H), 3.66 (s, 2H), 3.29 (d, 2H); ESI-MS m/z: 623[M+H]$^+$.

Example 27

Preparation of N-(3-chloro-4-((3-fluorobenzyl)oxy) phenyl)-6-(5-(((2-carboxypropyl)amino)methyl)-2-furyl)-4-quinazolinamine (MS25)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in (0.47 g, 1 mmol), was dissolved in tetrahydrofuran (10 ml), followed by the addition of isopropanol (2 ml) and threonine (0.23 g, 2 mmol), and stirred at room temperature for 6 h. Sodium triacetoxy borohydride (0.42 g, 2 mmol) was added, and then the mixture was stirred at room temperature for 48 h. 20% aqueous solution of sodium hydroxide (10 ml) was added and the mixture was stirred for 2 h, and then adjusted to PH~7 with hydrochloric acid. The organic layer was washed with saturated aqueous solution of sodium chloride, dried over anhydrous sodium sulfate, filtered, and rotary evaporated to give a yellow solid (0.32 g, 56.8%), i.e. the compound of Number MS25. m.p.: 153-155° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 3.75 (m, 2H), 3.65 (br, 1H), 3.58 (t, 1H); ESI-MS m/z: 563[M+H]$^+$.

Example 28

Preparation of N-(3-chloro-4-((3-fluorobenzyl)oxy) phenyl)-6-(5-((((1-carboxy-3-methylthio)propyl) amino)methyl)-2-furyl)-4-quinazolinamine (MS26)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in anhydrous tetrahydrofuran (10 ml), followed by the addition of methionine methyl ester hydrochloride (0.40 g, 2 mmol) and diisopropylethylamine (0.26 g, 2 mmol), and stirred at room temperature for 6 h. Sodium triacetoxy borohydride (0.74 g, 3.5 mmol) was added, and then the mixture was stirred at room temperature for 48 h. 20% aqueous solution of sodium hydroxide (10 ml) was added and the mixture was stirred for 2 h, and then adjusted to PH~7 with hydrochloric acid. The organic layer was washed with saturated aqueous solution of sodium chloride, dried over anhydrous sodium sulfate, filtered, and rotary evaporated to give a brown solid (0.30 g, 49.4%), i.e. the compound of Number MS26. m.p.: 131-133° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.66 (s, 2H), 3.59 (t, 1H), 2.60 (t, 2H), 2.14 (s, 3H), 1.91 (m, 2H); ESI-MS m/z: 607[M+H]$^+$.

Example 29

Preparation of N-(3-chloro-4-((3-fluorobenzyl)oxy) phenyl)-6-(5-(((2-hydroxyethyl)amino)methyl)-2-furyl)-4-quinazolinamine (MS27).dimethylsulfonate Under nitrogen, N-(3-chloro-4-((3-fluorobenzyl)oxy)phenyl)-6-(5-formyl-2-furyl)-4-quinazolinamine (5.69 g, 12 mmol) obtained from Example 1 was dissolved in tetrahydrofuran (100 ml), followed by the addition of ethanolamine (1.53 g, 25 mmol), and stirred at room temperature for 6 h. Sodium triacetoxy borohydride (8.48 g, 40 mmol) was added, and then the mixture was stirred at room temperature for 12 h. A saturated aqueous solution of sodium carbonate (50 ml) was added, and then the mixture was stirred for 15 min to be layered. The organic layer was washed with saturated aqueous solution of sodium chloride, dried over anhydrous sodium sulfate, filtered, and rotary evaporated to give a yellow powdered solid, i.e. the compound of Number MS27. The yellow powdered solid was dissolved in tetrahydrofuran (50 ml), and a solution of methanesulfonic acid (3.46 g, 36 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid (7.51 g, 88.0%), i.e. the dimethanesulfonate of the compound of Number MS27. m.p.: 263-265° C.; HPLC: >98.5%, $^1$H NMR (DMSO-$d_6$) $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.277.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 3.65 (br, 1H), 3.47 (m, 2H), 2.73 (d, 2H); ESI-MS m/z: 519[M+H]$^+$.

Example 30

Preparation of N-(3-chloro-4-((3-fluorobenzyl)oxy) phenyl)-6-(5-((((1-carboxy-2-hydroxy)ethyl)amino) methyl)-2-furyl)-4-quinazolinamine (MS28)

Preparation method of the example is the same as in Example 28, using serine as a starting material, TLC tracking to the end of the reaction. Under nitrogen, a yellow solid was obtained, i.e. the compound of Number MS28. m.p.: 153-155° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.84 (s, 2H), 3.75 (m, 2H), 3.65 (br, 1H), 3.58 (t, 1H); ESI-MS m/z: 563 [M+H]$^+$.

Example 31

Preparation of N-(3-chloro-4-((3-fluorobenzyl)oxy) phenyl)-6-(5-(((1-carboxy-2-mercapto)ethyl)amino) methyl)-2-furyl)-4-quinazolinamine (MS29)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of isopropanol (2 ml) and cysteine (0.24 g, 2 mmol), and stirred at room temperature for 6 h. Sodium triacetoxy borohydride (0.42 g, 2 mmol) was added, and then the mixture was stirred at room temperature for 48 h. 20% aqueous solution of sodium hydroxide (10 ml) was added and the mixture was stirred for 15 min, and then adjusted to PH~7 with hydrochloric acid. The organic layer was washed with saturated aqueous solution of sodium chloride, dried over anhydrous sodium sulfate, filtered, and rotary evaporated to give a yellow solid (0.32 g, 56.8%), i.e. the compound of Number MS29. m.p.: 146-149° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.99-4.04 (m, 1H), 3.81 (t, 1H), 3.66 (s, 2H), 2.79 (d, 2H); ESI-MS m/z: 579[M+H]$^+$.

Example 32

Preparation of N-(3-chloro-4-((3-fluorobenzyl)oxy) phenyl)-6-(5-((((1-carboxy-2-aminoformyl)ethyl) amino)methyl)-2-furyl)-4-quinazolinamine (MS30)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of isopropanol (2 ml) and asparagine (0.27 g, 2 mmol), and stirred at room temperature for 6 h. Sodium triacetoxy borohydride (0.42 g, 2 mmol) was added, and then the mixture was stirred at room temperature for 48 h. 20% aqueous solution of sodium hydroxide (10 ml) was added and the mixture was stirred for 15 min, and then adjusted to PH~7 with hydrochloric acid. The organic layer was washed with saturated aqueous solution of sodium chloride, dried over anhydrous sodium sulfate, filtered, and rotary evaporated to give a yellow solid (0.35 g, 59.3%), i.e. the compound of Number MS30. m.p.: 152-154° C.; $^1$H NMR (DMSO-$d_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.16 (s, 2H), 7.05 (d, J=3.2 Hz, 1H), 6.49 (d, J=3.3 Hz, 1H), 5.26 (s, 2H), 3.99-4.04 (m, 1H), 3.84 (s, 2H), 3.72 (t, 1H), 2.65 (d, 2H); ESI-MS m/z: 590[M+H]$^+$.

Example 33

Preparation of N-(3-chloro-4-((3-fluorobenzyl)oxy) phenyl)-6-(5-((1-(2,3-dihydroxypropyl)amino) methyl)-2-furyl)-4-quinazolinamine (MS31).dimethylsulfonate Under nitrogen, N-(3-chloro-4-((3-fluorobenzyl)oxy)phenyl)-6-(5-formyl-2-furyl)-4-quinazolinamine (5.69 g, 12 mmol) obtained from Example 1 was dissolved in tetrahydrofuran (100 ml), followed by the addition of 1-amino-2,3-propanediol (2.28 g, 25 mmol), and stirred at room temperature for 6 h. Sodium triacetoxy borohydride (8.48 g, 40 mmol) was added, and then the mixture was stirred at room temperature for 12 h. A saturated aqueous solution of sodium carbonate (50 ml) was added, and then the mixture was stirred for 15 min to be layered. The organic layer was washed with saturated aqueous solution of sodium chloride, dried over anhydrous sodium sulfate, filtered, and rotary evaporated to give a yellow powdered solid. The yellow powdered solid was dissolved in tetrahydrofuran (50 ml), and a solution of methanesulfonic acid (3.46 g, 36 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid (7.71 g, 86.7%), i.e. the dimethanesulfonate of the compound of Number MS31. HPLC: >98.5%, m.p.: 206-210° C.; $^1$H NMR (DMSO-$d_6$) δ: 8.49 (s, 1H), 8.22 (1H), 8.06 (1H), 8.05 (1H), 7.43 (1H), 7.36 (1H), 7.24 (d, 1H), 7.17 (1H), 7.01 (1H), 6.90 (m, 1H), 6.7 (1H), 6.68 (1H), 6.26 (1H), 5.16 (2H), 4.0 (1H), 3.81

(2H), 3.66 (2H), 3.65 (1H), 3.58 (1H), 3.54 (1H), 3.29 (6H), 2.83 (2H), 2.0 (3H); ESI-MS m/z: 549[M+H]$^+$.

Example 34

Preparation of N-(3-chloro-4-((3-fluorobenzyl)oxy) phenyl)-6-(5-((((4-carboxy-4-amino)butyl)amino) methyl)-2-furyl)-4-quinazolinamine (MS32)

Under nitrogen, N-(3-chloro-4-((3-fluorobenzyl)oxy)phenyl)-6-(5-formyl-2-furyl)-4-quinazolinamine (0.47 g, 1 mmol) obtained from Example 1 was dissolved in tetrahydrofuran (10 ml), followed by the addition of isopropyl (2 ml) and 2,5-diaminopentanoic acid (0.27 g, 2 mmol), and stirred at room temperature for 6 h. Sodium triacetoxy borohydride (0.42 g, 2 mmol) was added, and then the mixture was stirred at room temperature for 48 h. 20% aqueous solution of sodium hydroxide (10 ml) was added and the mixture was stirred for 15 min, and then adjusted to PH~7 with hydrochloric acid. The organic layer was washed with saturated aqueous solution of sodium chloride, dried over anhydrous sodium sulfate, filtered, and rotary evaporated to give a yellow solid (0.38 g, 64.4%), i.e. the compound of Number MS32. m.p.: 145-147° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 5.11 (s, 2H), 3.99-4.04 (m, 1H), 3.84 (s, 2H), 3.49 (m, 1H), 2.59 (m, 2H), 1.78 (m, 2H), 1.41 (m, 2H); ESI-MS m/z: 590[M+H]$^+$.

Example 35

Preparation of N-(3-chloro-4-((3-fluorobenzyl)oxy) phenyl)-6-(5-((morpholinyl)methyl)-2-thienyl)-4-quinazolinamine (MS33)

Under nitrogen, N-(3-chloro-4-((3-fluorobenzyl)oxy)phenyl)-6-(5-formyl-2-thienyl)-4-quinazolinamine (0.48 g, 1 mmol) prepared from Example 1 was dissolved in anhydrous tetrahydrofuran (10 ml), followed by the addition of morpholine (0.17 g, 2 mmol) and sodium triacetoxy borohydride (0.42 g, 2 mmol), and stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a solid with a color similar to yellow. The solid was separated by column chromatography on silica gel (200-300 mesh) (eluted with a gradient of ethyl acetate/methanol) to give a yellow solid (0.39 g, 71.5%), i.e. the compound of Number MS33. m.p.: 110-112° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 3.85 (s, 2H), 3.65 (t, 4H), 2.50 (t, 4H); ESI-MS m/z: 545[M+H]$^+$.

Example 36

Preparation of N-(3-chloro-4-((3-fluorobenzyl)oxy) phenyl)-6-(5-((4-methylpiperazinyl)methyl)-2-pyrrolidinyl)-4-quinazolinamine (MS34)

Under nitrogen, N-(3-chloro-4-((3-fluorobenzyl)oxy)phenyl)-6-(5-formyl-2-pyrrolidin)-4-quinazolinamine (0.47 g, 1 mmol) prepared from Example 1 was dissolved in anhydrous tetrahydrofuran (10 ml), followed by the addition of N-methylpiperazine (0.20 g, 2 mmol) and sodium triacetoxy borohydride (0.42 g, 2 mmol), and stirred at room temperature for 24 h. A saturated aqueous solution of sodium carbonate (10 ml) was added, and then the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.30 g, 53.8%), i.e. the compound of Number MS34. m.p.: 120-123° C.; $^1$H NMR (DMSO-d$_6$) δ: 9.87 (s, 1H), 8.74 (s, 1H), 8.56 (s, 1H), 8.16 (d, J=8.3 Hz, 1H), 8.01 (d, J=2.6 Hz, 1H), 7.79 (d, J=8.8 Hz, 1H), 7.74 (m, 1H), 7.46-7.49 (m, 1H), 7.27-7.35 (m, 3H), 7.18 (t, 1H), 7.05 (d, J=3.2 Hz, 1H), 6.49 (d, J=3.3 Hz, 1H), 5.26 (s, 2H), 5.0 (1H), 3.76 (s, 2H), 2.48 (t, 4H), 2.35 (t, 4H), 2.26 (s, 3H); ESI-MS m/z: 558[M+H]$^+$.

Example 37

Preparation of N-(3-chloro-4-((3-fluorobenzyl)oxy) phenyl)-6-(5-(((2-ethoxycarbonylethyl)amino) methyl)-2-furyl)-4-quinazolinamine (MS35).dimethylsulfonate Under nitrogen, the compound of Number MS27 (1.73 g, 2.3 mmol) prepared from Example 29, i.e. N-(3-chloro-4-((3-fluorobenzyl)oxy)phenyl)-6-(5-(((2-hydroxyethyl)amino)methyl)-2-furyl)-4-quinazolinamine.dimethanesulfonate, was dissolved in glacial acetic acid (20 ml), followed by the addition of concentrated sulfuric acid (1.0 ml), and stirred at room temperature for 12 h. The mixture was cooled down under stirring, and anhydrous ethanol (40 ml) was added to precipitate a dark yellow solid, i.e. the compound of Number MS35. The compound was filtered under suction, and the filter cake washed with anhydrous ethanol, alkalized in ethanol and salified with methanesulfonic acid, and then refined to give the dimethanesulfonate of the compound of Number MS35 (1.6 g), HPLC: >98.5%. 1H NMR (DMSO-d$_6$) $^1$H NMR (DMSO-d$_6$) δ: 8.49 (s, 1H), 8.22 (1H), 8.05 (2H), 7.36 (2H), 7.27 (d, 2H), 7.01 (1H), 6.90 (m, 1H), 6.7 (2H), 6.28 (1H), 5.16 (2H), 4.37 (2H), 4.0 (1H), 3.66 (2H), 3.29 (6H), 2.82 (2H), 2.21 (3H), 2.0 (3H) ESI-MS m/z: 527[M+H]$^+$.

Example 38

Preparation of intermediate N-(3-chloro-4-fluorophenyl)-6-(5-formyl-2-furyl)z-4-quinazolinamine To a reaction flask N-(3-chloro-4-fluorophenyl-6-iodo-4-quinazolinamine (19.99 g, 50 mmol), 5-formylfuran-2-boric acid (10.50 g, 75 mmol), 10% palladium on carbon (1.25 g, 54% water content), 1,2-dimethoxyethane (400 ml), methanol (200 ml) and triethylamine (21 ml, 150 mmol) were added. The mixture was heated to and kept at 50° C. and stirring for 24 h. The mixture was hot filtered under suction and the filtrate was rotary evaporated. To the residue was added methanol (150 ml) and water (50 ml). The mixture was stirred at 50° C. in a water bath for 30 min, and filtered under suction. The filter cake was washed sequentially with water and methanol, and dried under vacuum to afford an aurantiacus solid (22.6, 95.5%), i.e. the target product.

In the present invention, the compounds of Number MS36 to MS 41 can also be synthesized via the following reaction:

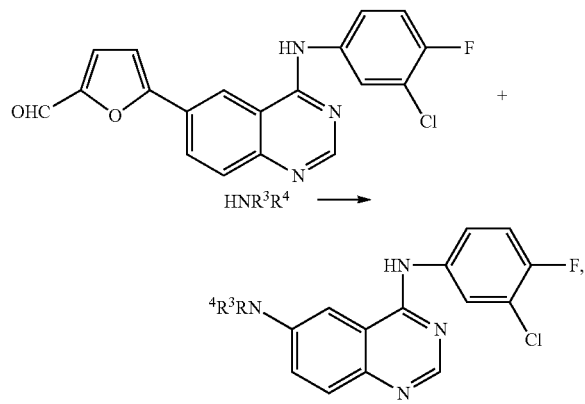

The preparation process of each compound of Number MS36 to MS41 would be described in detail in Example 39 to Example 44.

Example 39

Preparation of N-(3-chloro-4-fluorophenyl)-6-(5-(((propyl)amino)methyl)-2-furyl)-4-quinazolinamine (MS36)

Under nitrogen, N-(3-chloro-4-fluorophenyl)-6-(5-formyl-2-furyl)-4-quinazolinamine (0.37 g, 1 mmol) prepared from Example 38 was dissolved in anhydrous tetrahydrofuran (5 ml) and N,N'-dimethylformamide (5 ml), followed by the addition of propylamine (0.12 g, 2 mmol), and stirred at room temperature for 6 h. Sodium triacetoxy borohydride (0.42 g, 2 mmol) was added, and the mixture was stirred at room temperature for 24 h. After being rotary evaporated to dry, tetrahydrofuran (10 ml) and saturated aqueous solution of sodium carbonate (10 ml) were added, and the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.28 g, 68.1%), i.e. the compound of Number MS36. m.p.: 85-87° C.; $^1$H NMR (DMSO-$d_6$) δ: 9.87 (s, 1H), 8.73 (s, 1H), 8.46 (s, 1H), 8.25 (d, J=8.0 Hz, 1H), 7.95 (d, J=2.6 Hz, 1H), 7.73 (d, 1H), 7.44-7.49 (m, 1H), 7.15 (t, 1H), 7.02 (d, J=3.4 Hz, 1H), 6.29 (d, J=3.1 Hz, 1H), 3.97-4.04 (m, 1H), 3.67 (s, 2H), 2.59 (m, 2H), 1.46 (m, 2H), 0.93 (t, 3H); ESI-MS m/z: 411[M+H]$^+$.

Example 40

Preparation of N-(3-chloro-4-fluorophenyl)-6-(5-((((4-carboxy-4-amino)butyl)amino)methyl)-2-furyl)-4-quinazolinamine (MS37)

The preparation method of the Example was the same as in Example 39, using ornithine as a starting material, TLC tracking to the end of the reaction. A yellow solid was obtained under nitrogen, i.e. the compound of Number MS37. m.p.: 142-144° C.; $^1$H NMR (DMSO-$d_6$) δ: 9.87 (s, 1H), 8.73 (s, 1H), 8.46 (s, 1H), 8.25 (d, J=8.0 Hz, 1H), 7.95 (d, J=2.6 Hz, 1H), 7.73 (d, 1H), 7.44-7.49 (m, 1H), 7.15 (t, 1H), 7.02 (d, J=3.4 Hz, 1H), 6.29 (d, J=3.1 Hz, 1H), 5.26 (s, 2H), 3.97-4.04 (m, 1H), 3.84 (s, 2H), 3.49 (m, 1H), 2.59 (m, 2H), 1.78 (m, 2H), 1.41 (m, 2H); ESI-MS m/z: 484[M+H]$^+$.

Example 41

Preparation of N-(3-chloro-4-fluorophenyl)-6-(5-((((1-carboxy-4-amino)butyl)amino)methyl)-2-furyl)-4-quinazolinamine (MS38)

The preparation method of the Example was the same as in Example 39, using ornithine as a starting material, TLC tracking to the end of the reaction. A yellow solid was obtained under nitrogen, i.e. the compound of Number MS38. m.p.: 148-150° C.; $^1$H NMR (DMSO-$d_6$) δ: 9.87 (s, 1H), 8.73 (s, 1H), 8.46 (s, 1H), 8.25 (d, J=8.0 Hz, 1H), 7.95 (d, J=2.6 Hz, 1H), 7.73 (d, 1H), 7.44-7.49 (m, 1H), 7.15 (t, 1H), 7.02 (d, J=3.4 Hz, 1H), 6.29 (d, J=3.1 Hz, 1H), 5.11 (s, 2H), 3.97-4.04 (m, 1H), 3.85 (s, 2H), 3.52 (m, 1H), 2.65 (m, 2H), 1.68 (m, 2H), 1.51 (m, 2H); ESI-MS m/z: 484[M+H]$^+$.

Example 42

Preparation of N-(3-chloro-4-fluorophenyl)-6-(5-(((2-butenyl)amino)methyl)-2-furyl)-4-quinazolinamine (MS39)

Under nitrogen, N-(3-chloro-4-fluorophenyl)-6-(5-formyl-2-furyl)-4-quinazolinamine (0.37 g, 1 mmol) prepared from Example 38 was dissolved in anhydrous tetrahydrofuran (5 ml) and N,N'-dimethylformamide (5 ml), followed by the addition of (E)-2-butene-1-amine (0.14 g, 2 mmol), and stirred at room temperature for 6 h. Sodium triacetoxy borohydride (0.42 g, 2 mmol) was added, and the mixture was stirred at room temperature for 24 h. After being rotary evaporated to dry, tetrahydrofuran (10 ml) and saturated aqueous solution of sodium carbonate (10 ml) were added, and the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.26 g, 61.5%), i.e. the compound of Number MS39. m.p.: 92-94° C.; $^1$H NMR (DMSO-$d_6$) δ: 9.87 (s, 1H), 8.73 (s, 1H), 8.46 (s, 1H), 8.25 (d, J=8.0 Hz, 1H), 7.95 (d, J=2.6 Hz, 1H), 7.73 (d, 1H), 7.44-7.49 (m, 1H), 7.15 (t, 1H), 7.02 (d, J=3.4 Hz, 1H), 6.29 (d, J=3.1 Hz, 1H), 5.61 (m, 2H), 3.97-4.04 (m, 1H), 3.67 (s, 2H), 3.22 (s, 2H), 2.05 (s, 3H); ESI-MS m/z: 423[M+H]$^+$.

Example 43

Preparation of N-(3-chloro-4-fluorophenyl)-6-(5-(((2-(4-nitrophenyl)ethyl)amino)methyl)-2-furyl)-4-quinazolinamine (MS40)

Under nitrogen, N-(3-chloro-4-fluorophenyl)-6-(5-formyl-2-furyl)-4-quinazolinamine (0.37 g, 1 mmol) prepared from Example 38 was dissolved in anhydrous tetrahydrofuran (5 ml) and N,N'-dimethylformamide (5 ml), followed by the addition of 2-(4-nitrophenyl)ethylamine hydrochloride (0.41 g, 2 mmol) and diisopropylethylamine (0.26 g, 2 mmol), and the mixture was stirred at room temperature for 6 h. Sodium triacetoxy borohydride (0.42 g, 2 mmol) was added, and the mixture was stirred at room temperature for 24 h. After being rotary evaporated to dry, tetrahydrofuran (10 ml) and saturated aqueous solution of sodium carbonate (10 ml) were added, and the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.26 g, 61.5%), i.e. the compound of Number MS40. m.p.: 103-105° C.; $^1$H NMR (DMSO-$d_6$) δ: 0.87 (s, 1H), 8.73 (s, 1H), 8.46 (s, 1H), 8.21-8.25 (d, 3H), 7.95 (d, J=2.6 Hz, 1H), 7.73 (d, 1H), 7.44-7.55 (m, 3H), 7.15 (t, 1H), 7.02 (d, J=3.4 Hz, 1H), 6.29 (d, J=3.1 Hz, 1H), 3.97-4.04 (m, 1H), 3.67 (s, 2H), 2.84 (t, 2H), 2.64 (t, 2H); ESI-MS m/z: 518[M+H]$^+$.

Example 44

Preparation of N-(3-chloro-4-fluorophenyl)-6-(5-(((2-(cyclohexenyl)ethyl)amino)methyl)-2-furyl)-4-quinazolinamine (MS41)

Under nitrogen, N-(3-chloro-4-fluorophenyl)-6-(5-formyl-2-furyl)-4-quinazolinamine (0.37 g, 1 mmol) prepared from Example 38 was dissolved in anhydrous tetrahydrofuran (5 ml) and N,N'-dimethylformamide (5 ml), followed by the addition of 2-(1-cyclohexenyl)ethylamine (0.25 g, 2 mmol), and stirred at room temperature for 6 h. Sodium triacetoxy borohydride (0.42 g, 2 mmol) was added, and the mixture was stirred at room temperature for 24 h. After being rotary evaporated to dry, tetrahydrofuran (10 ml) and saturated aqueous solution of sodium carbonate (10 ml) were added, and the mixture was stirred for 15 min to be layered. The organic layer was washed with saturated aqueous solution of sodium chloride, dried over anhydrous sodium sulfate, filtered, and rotary evaporated to give a yellow solid. The solid was separated by column chromatography on silica gel (200-300 mesh) (eluted with a gradient of ethyl acetate/methanol) to give a yellow solid (0.27 g, 56.6%), i.e. the compound of Number MS41. m.p.: 91-93° C.; $^1$H NMR (DMSO-$d_6$) δ: 9.87 (s, 1H), 8.73 (s, 1H), 8.46 (s, 1H), 8.25 (d, J=8.0 Hz, 1H), 7.95 (d, J=2.6 Hz, 1H), 7.73 (d, 1H), 7.44-7.49 (m, 1H), 7.15 (t, 1H), 7.02 (d, J=3.4 Hz, 1H), 6.29 (d, J=3.1 Hz, 1H), 5.37 (t, 1H), 3.97-4.04 (m, 1H), 3.67 (s, 2H), 2.59 (t, 2H), 2.08 (t, 2H), 1.93 (t, 4H), 1.76 (t, 4H); ESI-MS m/z: 477[M+H]$^+$.

Example 45

Preparation of N-(3-chloro-4-((3-fluorobenzyl)oxy)phenyl)-6-(5-(((2-ethoxycarbonylethyl)amino)methyl)-2-furyl)-4-quinazolinamine (MS35).di-p-toluenesulfonate Under nitrogen, N-(3-chloro-4-((3-fluorobenzyl)oxy)phenyl)-6-(5-(((2-ethoxycarbonyl-ethyl)amino)methyl)-2-furyl)-4-quinazolinamine (5.4 g, 10 mmol), i.e. Number MS35, as a dark yellow solid prepared from Example 37 was dissolved in tetrahydrofuran (50 ml), and a solution of methanesulfonic acid (4.3 g, 25 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid (8.02 g, 89.4%), i.e. the di-p-toluenesulfonate of the compound of Number MS35.

Example 46

Preparation of N-(3-chloro-4-((3-fluorobenzyl)oxy)phenyl)-6-(5-(((3-hydroxypropyl)amino)methyl)-2-furyl)-4-quinazolinamine (MS42).di-p-toluenesulfonate The preparation method of the Example was the same as in Example 29, using propanolamine as a starting material, TLC tracking to the end of the reaction. Under nitrogen, a yellow powdered solid of N-(3-chloro-4-((3-fluorobenzyl)oxy)phenyl)-6-(5-(((3-hydroxypropyl)amino)methyl)-2-furyl)-4-quinazolinamine, i.e. the compound of Number MS42, was obtained. The compound of Number MS42 (5.1 g, 10 mmol) was dissolved in tetrahydrofuran (50 ml), A solution of methanesulfonic acid (4.3 g, 25 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid (7.65 g, 88.0%), i.e. the di-p-toluenesulfonate of the compound of Number MS42.

Example 47

Preparation of N-(3-chloro-4-((3-fluorobenzyl)oxy)phenyl)-6-(5-(((2-hydroxyethyl)amino)methyl)-2-furyl)-4-quinazolinamine (MS27).di-p-toluenesulfonate Under nitrogen, N-(3-chloro-4-((3-fluorobenzyl)oxy)phenyl)-6-(5-(((2-hydroxyethyl)amino)methyl)-2-furyl)-4-quinazolinamine (4.92 g, 10 mmol), i.e. the compound of Number MS27, as a yellow powdered solid prepared from Example 29 was dissolved in tetrahydrofuran (50 ml), and a solution of methanesulfonic acid (4.3 g, 25 mmol) in tetrahydrofuran (50 ml) was added dropwise under stirring. After the dropwise addition, the mixture was stirred at room temperature for 12 h. The mixture was filtered under suction and the filter cake was washed with tetrahydrofuran-deionized water (95:5). The product was refined, and dried at 70° C. under vacuum to give a yellow solid (7.50 g, 92.3%), i.e. the di-p-toluenesulfonate of the compound of Number MS27.

Example 48

Determining the Effect of Test Samples at a Concentration of 10-5 Mol/l on the Activity of the Substrate Phosphoryation Catalyzed by EGFR (Epidermal Growth Factor Receptor 1), ErbB-2 (Epidermal Growth Factor Receptor 2), ErbB-4, KDR (Vascular Endothelial Growth Factor Receptor 2) Protein Tyrosine Kinases at Molecular Level Enzyme-Linked Immunosorbent Assay (ELISA)
Main instrument: wavelength-tunable microplate reader (VERSAmax).
Main reagents: kinase reaction substrate Poly(Glu, Tyr) 4:1 from Sigma; anti-phosphotyrosine monoclonal antibody PY99 from Santa Cruz; horseradish peroxidase-labeled goat anti-mouse IgG from Calbiochem; ATP, DTT, OPD from Amresco, and ELISA plate from Corning.

Test Method:

Poly(Glu, Tyr)4:1 as an enzyme substrate was diluted by potassium ion-free PBS into 20 μg/ml, and an ELISA plate was coated and subjected to reaction for 12-16 h at 37° C. After the liquid in wells was removed, the plate was washed three time by T-PBS, 5 min for each time. The ELISA plate was then dried in an oven at 37° C. The coated wells were added with the test samples: the test samples were prepared for a stock solution with a concentration of $1\times10^{-2}$M in DMSO. The aliquot solution was stored at −20° C., and diluted to the desired concentration with reaction buffer before use. The resulting solution was added into the wells so that the final concentration of 10-5 mol/l in 100 μL reaction system can be obtained. At the same time, a positive control well was set up and a positive control compound Su11248 was added. ATP and test tyrosine kinases were added: ATP solution diluted with reaction buffer was added (the final concentration of ATP is 5 μM). Finally, the test tyrosine kinases solution diluted with reaction buffer was added. The total volume of the reaction system was 100 mL. Meanwhile, a negative control well and a control well without enzyme were set up. The reaction system was placed in a wet box, and shaked for 1 hour at 37° C., shielding from light. After the reaction was complete, the plate was washed by T-PBS three times. Antibody PY99 was added at 100 μL/well; and the plate was shaked for 30 min at 37° C. After the reaction was complete, the plate was washed with T-PBS three times. Horseradish peroxidase-labeled goat anti-mouse IgG was added at 100 μL/well, and the plate was shaked for 30 min at 37° C. The plate was washed with T-PBS three times. OPD developing liquid was added at 100 μL/well, and reacted for 1-10 min at room temperature, shielding from light. 50 μL of 2 M H2SO4 was added to stop the reaction. $A_{492}$ value was determined using wavelength-tunable microplate reader. The inhibition ratio of the samples can be calculated by the following equation:

$$\text{inhibition ratio \%} = \left(1 - \frac{OD \text{ value of compound} - OD \text{ value of control without enzyme}}{OD \text{ value of negative control} - OD \text{ value of control without enzyme}}\right) \times 100\%$$

The experimental results are shown in Table 1 below. The symbols in Table 1 are defined as follows: "+" indicating IC50<10 μM; "−" indicating IC50≥10 μM; "0" indicating that the compound did not screen out corresponding enzymes.

TABLE 1

Inhibitory activity of some compounds of the present invention against protein tyrosine kinases

| Compound Number | EGFR | KDR | ErbB2 | ErbB4 |
|---|---|---|---|---|
| MS1·dimethanesulfonate | + | + | + | + |
| MS 2 | + | 0 | − | 0 |
| MS 3 | + | 0 | + | 0 |
| MS 4 | + | 0 | + | 0 |
| MS5 | + | 0 | − | 0 |
| MS6·dimethanesulfonate | + | + | + | + |
| MS 7 | + | + | − | 0 |
| MS 8 | + | + | − | 0 |
| MS 9 | + | + | − | 0 |
| MS10·dimethanesulfonate | + | 0 | + | 0 |
| MS 11 | + | 0 | − | 0 |
| MS 12 | + | 0 | + | 0 |
| MS 13 | + | 0 | + | 0 |
| MS 14 | + | 0 | + | 0 |
| MS 15 | + | 0 | + | 0 |
| MS 16 | + | 0 | − | 0 |
| MS 17 | + | 0 | + | 0 |
| MS18·dimethanesulfonate | + | + | + | + |
| MS 19 | + | 0 | + | 0 |
| MS 20 | + | − | + | 0 |
| MS 21 | + | 0 | + | 0 |
| MS 22 | + | 0 | + | 0 |
| MS 23 | + | + | + | + |
| MS 24 | + | 0 | + | 0 |
| MS 25 | + | 0 | + | 0 |
| MS 26 | + | 0 | + | 0 |
| MS27·dimethanesulfonate | + | + | + | + |
| MS 28 | + | 0 | + | 0 |
| MS 29 | + | 0 | + | 0 |
| MS 30 | + | 0 | + | 0 |
| MS31·dimethanesulfonate | + | + | + | + |
| MS 32 | + | 0 | + | 0 |
| MS 33 | + | − | − | + |
| MS 34 | + | 0 | + | + |
| MS35·dimethanesulfonate | + | + | + | + |
| MS 36 | 0 | − | + | 0 |
| MS 37 | 0 | 0 | + | 0 |
| MS 38 | 0 | 0 | + | 0 |
| MS 39 | 0 | − | + | 0 |
| MS 40 | 0 | 0 | + | 0 |
| MS41 | 0 | − | + | 0 |
| MS35·di-p-toluenesulfonate | + | 0 | + | 0 |
| MS42·di-p-toluenesulfonate | + | + | + | + |
| MS27·di-p-toluenesulfonate | + | + | + | + |
| positive control: lapatinib | + | − | + | − |

As shown in Table 1:

1) Among a series of compounds provided in the present invention, most of them have better inhibition effect of EGFR, EGFR2;

2) Some compounds also possess very good inhibitory activity against KDR, ErbB4;

3) In particular, the compounds of MS1, MS6, MS18, MS23, MS27, MS31, MS35, MS42, etc. and pharmaceutically acceptable dimethanesulfonate or di-p-toluenesulfonate, possess higher inhibitory activity against KDR;

Example 49

Test of the Inhibition of Some Compounds of the Present Invention to the Growth of A549 Xenograft in Nude Mice Objective of the test: Determining the inhibition of some compounds of the present invention to the growth of human lung cancer A549 transplanted into nude mice and the action intensity thereof.

Experimental Method

1. Human lung cancer A549 xenograft in nude mice, which was set up by subcutaneously transplantation of the human lung cancer A549 cell lines into right axillary fossa of nude mice. The amount of inoculation is $2\times10^6$ cells/mouse. Xenograft inoculated into the nude mice was passaged for 3 generations before use.

2. The solvent used in the experiments is: 0.5% of hydroxypropylmethyl cellulose and 0.1% of Tween-80.

3. Vigorous growing tumor tissues were selected to be chopped into approximately 1 mm$^3$. Under sterile conditions, the tumor tissue blocks were subcutaneously transplanted into right axillary fossa of nude mice. The diameters of the xenograft in nude mice were measured with a vernier caliper. When tumors reached approximately 100-300 mm$^3$ in size, the animals were randomly divided into groups, wherein there are 12 animals in solvent control group, and 6 animals per group in the other groups. By means of measuring the diameters of the tumors, the anti-tumor effect of the test compounds was dynamically observed. The test compounds and positive medicant lapatinib were both administrated intragastric administration. The administered dosages were both 200 mg/kg, 5 times per week for consecutive four weeks. The diameters of the tumors were measured twice per week. The negative control group was intragastricly administered the same amount of solvent. After the experiment, the mice were sacrificed. The tumors were surgically stripped and weighed. The tumor volume (TV) was calculated by the following equation:

$$TV = \frac{1}{2} \times a \times b^2,$$

in which a and b represents for the length and the width respectively.

According to the measured results, the relative tumor volume (RTV) was calculated. The calculation equation was: $RTV=V_t/V_0$, wherein $V_0$ is the tumor volume measured during cage administration (i.e. $d_0$), $V_t$ is the tumor volume of each measurement. The evaluation index of anti-tumor activity was the relative tumor growth ratio T/C (%), which was calculated by the following equation:

$$T/C(\%) = \frac{T_{RTV}}{C_{RTV}} \times 100$$

$T_{RTV}$: treatment group's RTV; $C_{RTV}$: negative control group's RTV.

Results of the test are shown in Table 2 below.

TABLE 2

The growth inhibition of some compounds of the present invention to A549 xenograft in nude mice

| Group | Dosage | Number of animals Start | Number of animals End | Weight (g) Start | Weight (g) End | TV (mm$^3$) Start | TV (mm$^3$) End | T/C (%) |
|---|---|---|---|---|---|---|---|---|
| Control group | 0.1 ml/10 g | 12 | 12 | 25.5 ± 2.1 | 27.8 ± 1.4 | 155.3 ± 88.3 | 2129.5 ± 384.2 | — |
| Lapatinib (positive medicament) | 200 mg/kg | 6 | 6 | 24.1 ± 2.9 | 26.3 ± 3.3 | 153.6 ± 64.8 | 943.2 ± 225.7▲ | 45.1 |
| M527•dimethanesulfonate | 200 mg/kg | 6 | 6 | 25.0 ± 2.7 | 25.6 ± 2.2 | 155.3 ± 71.2 | 775.6 ± 215.4▲ | 36.4 |
| MS6•dimethanesulfonate | 200 mg/kg | 6 | 6 | 24.9 ± 1.3 | 25.2 ± 1.4 | 156.9 ± 64.5 | 844.5 ± 240.3▲ | 39.3 |
| MS23 | 200 mg/kg | 6 | 6 | 25.3 ± 1.5 | 25.7 ± 2.0 | 153.5 ± 74.8 | 804.3 ± 230.3▲ | 38.2 |
| MS36 | 200 mg/kg | 6 | 6 | 24.5 ± 1.8 | 25.0 ± 1.8 | 155.5 ± 72.8 | 770.3 ± 212.8▲ | 36.1 |

Note:
▲$p < 0.01$ VS Control

It is further shown according to Table 2 that the compounds of the present invention, particularly MS6, MS23, MS27, MS36, have better growth inhibition effect on the human lung cancer A549 than positive control lapatinib.

Example 50

Test of the Inhibition of Some Compounds of the Present Invention to the Growth of NCI-H1975 Xenograft in Nude Mice Administration route: intragastric administration. Administration volume: 0.1 ml/10 g. Administration and frequency: administrating for 5 consecutive days and suspending administration for two days weekly for four weeks. Observation time: continuous observation for 28 days after starting administration. The tumor volume was measured twice a week. At the end of the experiment, the animals were sacrificed, weighed and photographed. Statistical method: SPSS 10.0 statistical software package, one-factor analysis of variance. The other methods can be found in Example 49.

TABLE 3

Experimental research on the effect of a series of MS7203 modifications on the growth of NC1-H1975 xenograft in nude mice

| Group | Number of animals | | Tumor volume (mm³) | | T/C (%) |
|---|---|---|---|---|---|
| | D 0 | D 28 | D 0 | D 28 | |
| Vehicle | 9 | 9 | 95.00 ± 27.16 | 2433.29 ± 1319.22 | / |
| MS27·dimethanesulfonate | 7 | 7 | 97.06 ± 38.91 | 1214.25 ± 944.16★ | 49.8★ |
| Lapatinib | 7 | 7 | 90.64 ± 16.08 | 2420.50 ± 1405.01 | 104.26 |
| Gefitinib | 7 | 7 | 95614 ± 49.67 | 2164.44 ± 1064.85 | 87.89 |

Note:
1) ★P < 0.01 VS Vehicle; * P < 0.05 VS Vehicle.

NC1-H1975 is a tumor cell line with gene mutation, which can produce medicament resistant to lapatinib. Gefitinib has almost no activity either, but MS27.dimethanesulfonate still exhibited good activity.

The invention claimed is:

1. Compounds represented by the following structural general formula (I) or pharmaceutically acceptable salts thereof:

wherein $R^1$ is

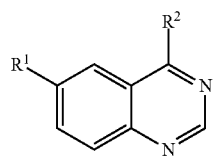

(I)

A is O,

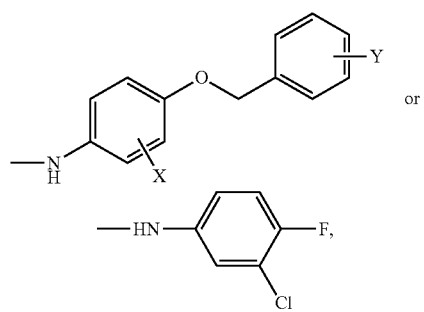

$R^2$ is

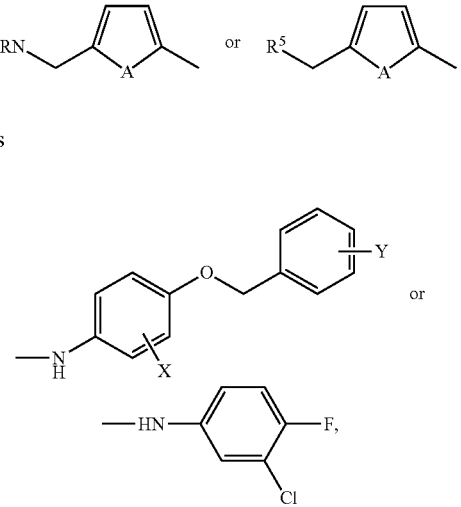

X and Y are independently selected from the group consisting of halogen, fluoro, chloro, and bromo;

$R^3$ and $R^4$ are independently chosen from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

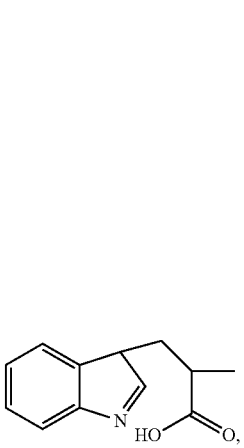

wherein said substituents are one or more groups chosen from nitro, carboxy, halogen atoms, hydroxy, $C_{1-6}$ alkoxy, ester group, $C_{1-6}$ alkoxycarbonyl, $C_{1-6}$ alkanoyloxy, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, or optionally substituted heteroaryl $C_{1-6}$ alkoxy, wherein said substituent on the aryl or heteroaryl group is one or more group chosen from, hydroxy, mercapto, amino, nitro, halogen atoms, $C_{1-6}$ alkyl, $C_{1-6}$ alkoxy, $C_{1-6}$ alkylthio, or carboxy;

$R^5$ is a 3- to 8- membered heterocyclic group containing at least one heteroatom chosen from N, O, or S, which is optionally substituted by $R^6$, wherein said $R^6$ is chosen from H, $C_{1-6}$ alkyl, halo-$C_{1-6}$ alkyl, or hydroxy-$C_{1-6}$ alkyl;

excluding

N-(4-(3-fluorobenzyloxy)-3-chlorophenyl)-6-(5-(morpholinyl-methyl)-2-furyl)quinazolin-4-amine;

N-(4-(3-fluorobenzyloxy)-3-chlorophenyl)-6-(5-(4-methylpiperazinyl-1-methyl)-2-furyl)-quinazolin-4-amine;

N-(4-(3-fluorobenzyloxy)-3-chlorophenyl)-6-(5-(piperazinyl-1-methyl)-2-furyl)quinazolin-4-amine; and N-(4-(3-fluorobenzyloxy)-3-chlorophenyl)-6-(5-((2-(methylthio)ethylamino)methyl-2-furyl)quinazolin-4-amine.

2. The compounds or pharmaceutically acceptable salts thereof according to claim 1, wherein $R^2$ is X is fluoro, chloro or bromo, Y is fluoro, chloro or bromo;
$R^3$ and $R^4$ are independently chosen from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

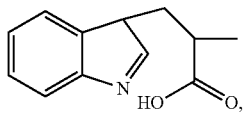

wherein said substituents are one or more groups chosen from nitro, carboxy, halogen atoms, hydroxy, $C_{1-6}$ alkoxy, ester group, $C_{1-6}$ alkoxycarbonyl, $C_{1-6}$ alkanoyloxy, $C_{2-6}$ alkenoxycarbonyl, $C_{2-6}$ alkenoyloxy, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, optionally substituted heteroaryl $C_{1-6}$ alkoxy, wherein said substituent on the aryl or heteroaryl group is one or more group chosen from hydroxy, mercapto, amino, nitro, halogen atoms, $C_{1-6}$ alkyl, $C_{1-6}$ alkoxy, $C_{1-6}$ alkylthio, or carboxy;

$R^5$ is

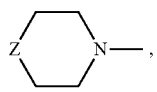

in which Z is S, O or $NR^6$, wherein said $R^6$ is H or $C_{1-6}$ alkyl.

3. The compounds or pharmaceutically acceptable salts thereof according to claim 1, wherein
$R^2$ is

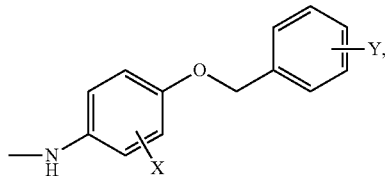

wherein X is fluoro, chloro or bromo, Y is fluoro, chloro or bromo;

$R^3$ is $C_{1-10}$ alkyl, $C_{2-10}$ unsaturated alkenyl, $C_{2-10}$ unsaturated alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

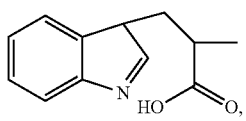

wherein said substituents are one or more groups chosen from nitro, carboxy, halogen atoms, hydroxy, methoxy, ethoxycarbonyl, methoxycarbonyl, aminocarbonyl, optionally substituted phenyl, optionally substituted benzyl, or optionally substituted benzyloxy, wherein the substituent on the phenyl group is one or more group chosen from hydroxy, methoxy, nitro, fluoro, chloro, or bromo;

$R^4$ is H or $C_{1-6}$ alkyl;

$R^5$ is

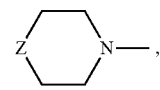

in which Z is S, O or $NR^6$, wherein said $R^6$ is H or $C_{1-6}$ alkyl.

4. The compounds or pharmaceutically acceptable salts thereof according to claim 1, wherein:
$R^2$ is

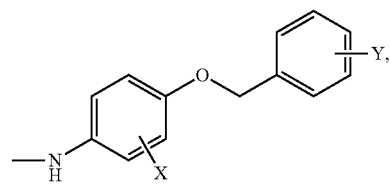

X is chloro and Y is fluoro, $R^3$ is $C_{1-10}$ alkyl, $C_{2-10}$ alkenyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, or

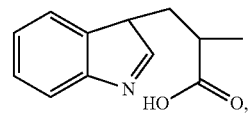

wherein the substituent is one or more group chosen from nitro, carboxy, halogen atoms, hydroxy, methoxy, ethoxycarbonyl, methoxycarbonyl, aminocarbonyl, optionally substituted phenyl, optionally substituted benzyl, or optionally substituted benzyloxy, wherein the substituent on the phenyl group is one or more group chosen from hydroxy, methoxy, nitro, fluoro, chloro, or bromo;

$R^4$ is H or $C_{1-4}$ alkyl;
$R^5$ is

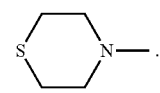

5. The compounds or pharmaceutically acceptable salts thereof according to claim 1, wherein $R^3$ is chosen from the following structures and optical isomers thereof:

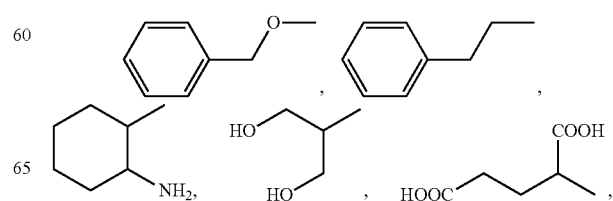

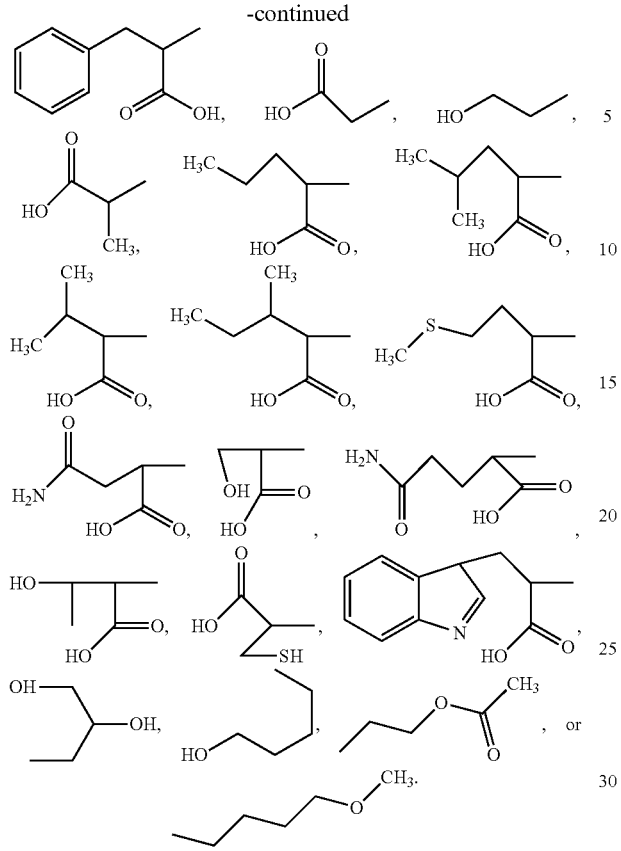

6. The compounds or pharmaceutically acceptable salts thereof according to claim 1, wherein each of the compounds is selected from the group consisting of Number MS1:
- N-(3-chloro-4-((3-fluorobenzyl)oxy)phenyl)-6-(5-((4-hydroxybutyl)amino)methyl-2-furyl)-4-quinazolinamine;
- N-(3-chloro-4-(3-fluorobenzyl)oxy)phenyl)-6-(5-((3-phenylpropyl)amino)methyl)-2-furyl)-4-quinazolinamine;

Number MS2:
- N-(3-chloro-4-((3-fluorobenzyl)oxy)phenyl)-6-(5-((n-hexylamino)methyl)-2-furyl)-4-quinazolinamine;

Number MS3:
- N-(3-chloro-4-((3-fluorobenzyl)oxy)phenyl)-6-(5-((ethylamino)methyl)-2-furyl)-4-quinazolinamine;

Number MS4:
- N-(3-chloro-4-((3-fluorobenzyl)oxy)phenyl)-6-(5-((N,N-diethyl)amino)methyl)-2-furyl)-4-quinazolinamine;

Number MS5:
- N-(3-chloro-4-((3-fluorobenzyl)oxy)phenyl)-6-(5-(((2-butenyl)amino)methyl)-2-furyl)-4-quinazolinamine;

Number MS6:
- N-(3-chloro-4-((3-fluorobenzyl)oxy)phenyl)-6-(5-((2-(1,3-dihydroxypropyl)amino)methyl)-2-furyl)-4-quinazolinamine;

Number MS7:
- N-(3-chloro-4-(3-fluorobenzyl)oxy)phenyl)-6-((5-((cyclohexylmethyl)amino)methyl)-2-furyl)-4-quinazolinamine;

Number MS8:
- N-(3-chloro-4-((3-fluorobenzyl)oxy)phenyl)-6-(5-(((2-(3-cyclohexenyl)ethyl)amino)methyl)-2-furyl)-4-quinazolinamine;

Number MS9:
- N-(3-chloro-4-(3-fluorobenzyl)oxy)phenyl)-6-(5-((((3-chlorocyclohexyl)methyl)amino)methyl)-2-furyl)-4-quinazolinamine;

Number MS 10:
- N-(3-chloro-4-((3-fluorobenzyl)oxy)phenyl)-6-(5-(((4-methoxybutyl)amino)methyl)-2-furyl)-4-quinazolinamine;

Number MS 11:
- N-(3-chloro-4-((3-fluorobenzyl)oxy)phenyl)-6-(5-(((3-chlorobenzyl)amino)methyl)-2-furyl)-4-quinazolinamine;

Number MS 12:
- N-(3-chloro-4-((3-fluorobenzyl)oxy)phenyl)-6-(5-(((2-(4-nitrophenyl)ethyl)amino)methyl)-2-furyl)-4-quinazolinamine;

Number MS13:
- N-(3-chloro-4-((3-fluorobenzyl)oxy)phenyl)-6-(5-(((2-(4-hydroxyphenyl)ethyl)amino)methyl)-2-furyl)-4-quinazolinamine;

Number MS 14:
- N-(3-chloro-4-((3-fluorobenzyl)oxy)phenyl)-6-(5-(((2-(3,5-dimethoxyphenyl)ethylamino)methyl)-2-furyl)-4-quinazolinamine;

Number MS15:
- N-(3-chloro-4-((3-fluorobenzyl)oxy)phenyl)-6-(5-(((2-(3-hydroxy-5-fluorophenyl)ethyl)amino)methyl)-2-furyl)-4-quinazolinamine;

Number MS 16:
- N-(3-chloro-4-((3-fluorobenzyl)oxy)phenyl)-6-(5-(((2-(3-chloro-5-fluorophenyl)ethyl)amino)methyl)-2-furyl)-4-quinazolinamine;

Number MS 17:
- N-(3-chloro-4-((3-fluorobenzyl)oxy)phenyl)-6-(5-(((2-,6-dihydroxyhexyl)amino)methyl)-2-furyl)-4-quinazolinamine;

Number MS 18:
- N-(3-chloro-4-((3-fluorobenzyl)oxy)phenyl)-6-(5-((bis(2-hydroxyethyl)amino)methyl)-2-furyl)-4-quinazolinamine;

Number MS 19:
- N-(3-chloro-4-((3-fluorobenzyl)oxy)phenyl)-6-(5-(((benzyloxy)amino)methyl)-2-furyl)-4-quinazolinamine;

Number MS20:
- N-(3-chloro-4-((3-fluorobenzyl)oxy)phenyl)-6-(5-(((2-(3-chlorophenyl)ethyl)amino)methyl)-2-furyl)-4-quinazolinamine;

Number MS21:
- N-(3-chloro-4-(3-fluorobenzyl)oxy)phenyl)-6-(5-(((3-aminocyclohexyl)amino)methyl)-2-furyl)-4-quinazolinamine;

Number MS22:
- N-(3-chloro-4-((3-fluorobenzyl)oxy)phenyl)-6-(5-(((carboxymethyl)amino)methyl)-2-furyl)-4-quinazolinamine;
- N-(3-chloro-4-((3-fluorobenzyl)oxy)phenyl)-6-(5-(((1-carboxyethyl)amino)methyl)-2-furyl)-4-quinazolinamine;
- N-(3-chloro-4-((3-fluorobenzyl)oxy)phenyl)-6-(5-(((1-carboxybutyl)amino)methyl)-2-furyl)-4-quinazolinamine;
- N-(3-chloro-4-((3-fluorobenzyl)oxy)phenyl)-6-(5-(((1-carboxy-3-methylbutyl)amino)methyl)-2-furyl)-4-quinazolinamine;
- N-(3-chloro-4-((3-fluorobenzyl)oxy)phenyl)-6-(5-(((1-carboxy-2-methylpropyl)amino)methyl)-2-furyl)-4-quinazolinamine;

N-(3-chloro-4-((3-fluorobenzyl)oxy)phenyl)-6-(5-(((1-carboxy-2-methylbutyl)amino)methyl)-2-furyl)-4-quinazolinamine;

N-(3-chloro-4-((3-fluorobenzyl)oxy)phenyl)-6-(5-(((1-carboxy-4-amino-4-oxobutyl)amino)methyl)-2-furyl)-4-quinazolinamine;

N-(3-chloro-4-((3-fluorobenzyl)oxy)phenyl)-6-(5-(((1-carboxy-2-hydroxypropyl)amino)methyl)-2-furyl)-4-quinazolinamine;

N-(3-chloro-4-(3-fluorobenzyl)oxy)phenyl)-6-(5-(((1-carboxy-3-(3H-indol-3-yl)propyl)amino)methyl)-2-furyl)-4-quinazolinamine;

Number MS23:
N-(3-chloro-4-((3-fluorobenzyl)oxy)phenyl)-6-(5-(((1,3-dicarboxypropyl)amino)methyl)-2-furyl)-4-quinazolinamine;

Number MS24:
N-(3-chloro-4-((3-fluorobenzyl)oxy)phenyl)-6-(5-((((1-carboxy-2-phenyl)ethyl)amino)methyl)-2-furyl)-4-quinazolinamine;

Number MS25:
N-(3-chloro-4-((3-fluorobenzyl)oxy)phenyl)-6-(5-(((2-carboxypropyl)amino)methyl)-2-furyl)-4-quinazolinamine;

Number MS26:
N-(3-chloro-4-((3-fluorobenzyl)oxy)phenyl)-6-(5-((((1-carboxy-3-methylthio)propyl)amino)methyl)-2-furyl)-4-quinazolinamine;

Number MS27:
N-(3-chloro-4-((3-fluorobenzyl)oxy)phenyl)-6-(5-(((2-hydroxyethyl)amino)methyl)-2-furyl)-4-quinazolinamine;

Number MS28:
N-(3-chloro-4-((3-fluorobenzyl)oxy)phenyl)-6-(5-((((1-carboxy-2-hydroxy)ethyl)amino)methyl)-2-furyl)-4-quinazolinamine;

Number MS29:
N-(3-chloro-4-((3-fluorobenzyl)oxy)phenyl)-6-(5-(((1-carboxy-2-mercapto)ethyl)amino)methyl)-2-furyl)-4-quinazolinamine;

Number MS30:
N-(3-chloro-4-((3-fluorobenzyl)oxy)phenyl)-6-(5-((((1-carboxy-2-aminoformyl)ethyl)amino)methyl)-2-furyl)-4-quinazolinamine;

Number MS31:
N-(3-chloro-4-((3-fluorobenzyl)oxy)phenyl)-6-(5-(1-(2,3-dihydroxypropyl)amino)methyl-2-furyl)-4-quinazolinamine;

Number MS32:
N-(3-chloro-4-((3-fluorobenzyl)oxy)phenyl)-6-(5-((((4-carboxy-4-amino)butyl)amino)methyl)-2-furyl)-4-quinazolinamine;

Number MS33:
N-(3-chloro-4-(3-fluorobenzyl)oxy)phenyl)-6-(5-((morpholinyl)methyl)-2-thienyl)-4-quinazolinamine;

Number MS34:
N-(3-chloro-4-((3-fluorobenzyl)oxy)phenyl)-6-(5-((4-methylpiperazinyl)methyl)-2-pyrrolidinyl)-4-quinazolinamine; or Number MS35:
N-(3-chloro-4-((3-fluorobenzyl)oxy)phenyl)-6-(5-(((2-ethoxycarbonylethyl)amino)methyl)-2-furyl)-4-quinazolinamine;

N-(3-chloro-4-(3-fluorobenzyl)oxy)phenyl)-6-(5-(((2-hydroxyethyl)amino)methyl)-2-furyl)-4-quinazolinamine.dimethylsulfonate;

N-(3-chloro-4-((3-fluorobenzyl)oxy)phenyl)-6-(5-((2-(1,3-dihydroxypropyl)amino)methyl)-2-furyl)-4-quinazolinamine.dimethylsulfonate;

N-(3-chloro-4-((3-fluorobenzyl)oxy)phenyl)-6-(5-(((2-ethoxycarbonylethyl)amino)methyl)-2-furyl)-4-quinazolinamine.dimethylsulfonate;

N-(3-chloro-4-((3-fluorobenzyl)oxy)phenyl)-6-(5-((bis(2-hydroxyethyl)amino)methyl)-2-furyl)-4-quinazolinamine.dimethylsulfonate;

N-(3-chloro-4-((3-fluorobenzyl)oxy)phenyl)-6-(5-((4-hydroxybutyl)amino)methyl-2-furyl)-4-quinazolinamine.dimethylsulfonate;

N-(3-chloro-4-((3-fluorobenzyl)oxy)phenyl)-6-(5-(1-(2,3-dihydroxypropyl)amino)methyl-2-furyl)-4-quinazolinamine.dimethylsulfonate;

N-(3-chloro-4-((3-fluorobenzyl)oxy)phenyl)-6-(5-(((4-methoxybutyl)amino)methyl)-2-furyl)-4-quinazolinamine.dimethylsulfonate;

N-(3-chloro-4-((3-fluorobenzyl)oxy)phenyl)-6-(5-(((2-ethoxycarbonylethyl)amino)methyl)-2-furyl)-4-quinazolinamine.di-p-toluenesulfonate;

N-(3-chloro-4-((3-fluorobenzyl)oxy)phenyl)-6-(5-(((3-hydroxypropyl)amino)methyl)-2-furyl)-4-quinazolinamine.di-p-toluenesulfonate; and N-(3-chloro-4-((3-fluorobenzyl)oxy)phenyl)-6-(5-(((2-hydroxyethyl)amino)methyl)-2-furyl)-4-quinazolinamine.di-p-toluenesulfonate.

7. Compounds of general formula (I) or pharmaceutically acceptable salts thereof

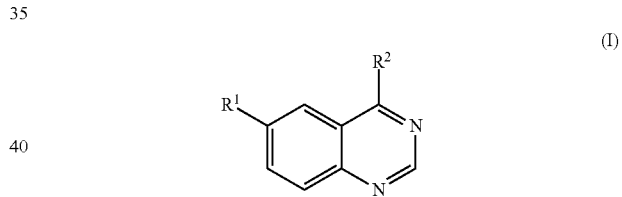

(I)

wherein $R^1$ is

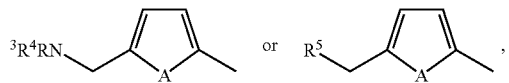

A is O, S, $NR^7$, wherein $R^7$ is H or $C_{1-6}$ alkyl;

$R^2$ is

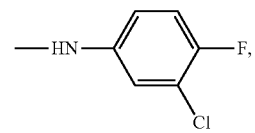

$R^3$ and $R^4$ are each independently chosen from H, $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

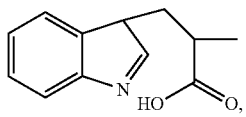

wherein said substituents are one or more groups chosen from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, or optionally substituted heteroaryl $C_{1-6}$ alkoxy, wherein said substituent on the aryl or heteroaryl group is one or more group chosen from hydroxy, mercapto, amino, nitro, halogen, $C_{1-6}$ alkyl, $C_{1-6}$ alkoxy, or $C_{1-6}$ alkylthio, carboxy;

$R^5$ is a 3- to 8- membered heterocyclic group containing at least one heteroatom chosen from N, O, or S, which is optionally substituted by $R^6$, wherein said $R^6$ is H, $C_{1-6}$ alkyl, halo-$C_{1-6}$ alkyl, or hydroxy-$C_{1-6}$ alkyl.

8. The compounds or pharmaceutically acceptable salts thereof according to claim 7, wherein
$R^3$ and $R^4$ are independently chosen from H, $C_{1-10}$ alkyl, $C_{2-10}$ alkenyl, $C_{3-10}$ cycloalkyl with substituents, $C_{3-10}$ cycloalkenyl with substituents, $C_{1-10}$ alkyl with substituents, $C_{2-10}$ alkenyl with substituents, or

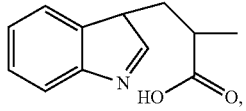

wherein said substituents are one or more groups chosen from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted aryl, optionally substituted heteroaryl, optionally substituted aryl $C_{1-6}$ alkyl, optionally substituted heteroaryl $C_{1-6}$ alkyl, optionally substituted aryloxy, optionally substituted heteroaryloxy, optionally substituted aryl $C_{1-6}$ alkoxy, or optionally substituted heteroaryl $C_{1-6}$ alkoxy, wherein said substituent on the aryl or heteroaryl group is one or more group chosen from hydroxy, mercapto, amino, nitro, halogen, $C_{1-6}$ alkyl, $C_{1-6}$ alkoxy, $C_{1-6}$ alkylthio, or carboxy;

$R^5$ is a 3- to 8- membered heterocyclic group containing at least one heteroatom chosen from N, O, or S, which is optionally substituted by $R^6$, wherein said $R^6$ is H, $C_{1-6}$ alkyl, halo-$C_{1-6}$ alkyl, or hydroxy-$C_{1-6}$ alkyl.

9. The compounds or pharmaceutically acceptable salts thereof according to claim 7, wherein
$R^3$ is chosen from $C_{1-10}$ alkyl, $C_{2-10}$ alkenyl, $C_{2-10}$ alkynyl, $C_{3-10}$ cycloalkyl, $C_{1-10}$ alkyl with substituents, $C_{2-10}$ alkenyl with substituents, $C_{3-10}$ cycloalkyl with substituents, $C_{3-10}$ cycloalkenyl with substituents, $C_{1-10}$ ether or

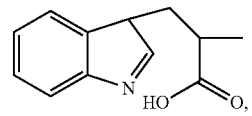

wherein said substituents are one or more groups chosen from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted phenyl, optionally substituted benzyl, or optionally substituted benzyloxy, wherein said substituent on the benzene ring is one or more group chosen from hydroxy, mercapto, amino, nitro, halogen, $C_{1-6}$ alkyl, $C_{1-6}$ alkoxy, $C_{1-6}$ alkylthio, or carboxy;

$R^4$ is H or $C_{1-6}$ alkyl;

$R^5$ is a 3- to 8- membered heterocyclic group containing at least one heteroatom chosen from N, S, or O, which is connected to a methylene group via N atom, and $R^5$ is optionally substituted by $R^6$, wherein said $R^6$ is H, $C_{1-6}$ alkyl, halo $C_{1-6}$ alkyl, or hydroxy $C_{1-6}$ alkyl.

10. The compounds or pharmaceutically acceptable salts thereof according to claim 7, wherein
$R^3$ is selected from $C_{2-10}$ alkenyl with substituents, $C_{1-10}$ alkyl with substituents, $C_{3-10}$ cycloalkyl with substituents, $C_{3-10}$ cycloalkenyl with substituents, or

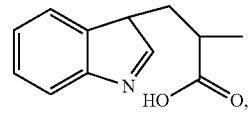

wherein said substituents are one or more groups chosen from nitro, amino, carboxy, halogen atoms, hydroxy, mercapto, $C_{1-6}$ alkylthio, $C_{1-6}$ alkoxy, ester group, $C_{1-6}$ alkoxycarbonyl, $C_{1-6}$ alkanoyloxy, amide group, aminocarbonyl, $C_{1-6}$ alkylaminocarbonyl, di($C_{1-6}$ alkyl)aminocarbonyl, optionally substituted phenyl, optionally substituted benzyl, or optionally substituted benzyloxy, wherein said substituent on the benzene ring is one or more group chosen from hydroxy, mercapto, amino, nitro, halogen, $C_{1-6}$ alkyl, $C_{1-6}$ alkoxy, $C_{1-6}$ alkylthio, or carboxy;

$R^4$ is H or $C_{1-4}$ alkyl;

$R^5$ is

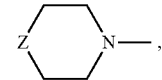

in which Z is S, O or $NR^6$, wherein said $R^6$ is H or $C_{1-6}$ alkyl.

11. The compounds or pharmaceutically acceptable salts thereof according to claim 7, wherein each of the compounds is selected from the group consisting of Number MS36:
N-(3-chloro-4-fluorophenyl)-6-(5-(((propyl)amino)methyl)-2-furyl)-4-quinazolinamine;
Number MS37:
N-(3-chloro-4-fluorophenyl)-6-(5-((((4-carboxy-4-amino)butyl)amino)methyl)-2-furyl)-4-quinazolinamine;

Number MS38:
N-(3-chloro-4-fluorophenyl)-6-(5-((((1-carboxy-4-amino)butyl)amino)methyl)-2-furyl)-4-quinazolinamine;
Number MS39:
N-(3-chloro-4-fluorophenyl)-6-(5-(((2-butenyl)amino)methyl)-2-furyl)-4-quinazolinamine;
Number MS40:
N-(3-chloro-4-fluorophenyl)-6-(5-(((2-(4-nitrophenyl)ethyl)amino)methyl)-2-furyl)-4-quinazolinamine;
Number MS41:
N-(3-chloro-4-fluorophenyl)-6-(5-(((2-(cyclohexenyl)ethyl)amino)methyl)-2-furyl)-4-quinazolinamine; and
Number MS42:
N-(3-chloro-4-((3-fluorobenzyl)oxy)phenyl)-6-(5-(((3-hydroxypropyl)amino)methyl)-2-furyl)-4-quinazolinamine.

12. Compounds represented by general formula (I) or pharmaceutically acceptable salts thereof:

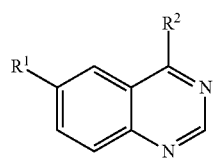

(I)

wherein R¹ is

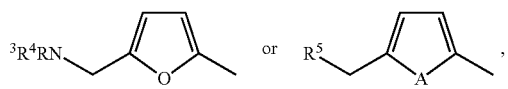

A is S or NR⁷, in which R⁷ is H or C₁₋₆ alkyl,
R² is

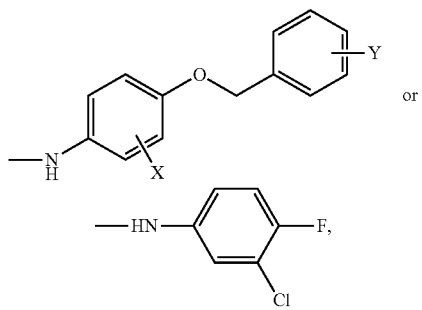

X and Y are independently selected from a group consisting of halogen, fluoro, chloro, and bromo,
R³ and R⁴ are independently chosen from H, C₁₋₁₀ alkyl, C₂₋₁₀ alkenyl, C₂₋₁₀ alkynyl, C₃₋₁₀ cycloalkyl, C₁₋₁₀ alkyl with substituents, C₂₋₁₀ alkenyl with substituents, C₃₋₁₀ cycloalkyl with substituents, C₃₋₁₀ cycloalkenyl with substituents, C₁₋₁₀ ether or

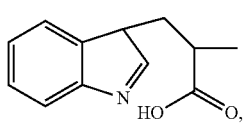

wherein said substituents are one or more groups chosen from nitro, amino, carboxy, halogen atoms, hydroxy, mercapto, C₁₋₆ alkylthio, C₁₋₆ alkoxy, ester group, C₁₋₆ alkoxycarbonyl, C₁₋₆ alkanoyloxy, amide group, aminocarbonyl, C₁₋₆ alkylaminocarbonyl, di(C₁₋₆ alkyl)aminocarbonyl, optionally substituted aryl, optionally substituted heteroaryl, optionally substituted aryl C₁₋₆ alkyl, optionally substituted heteroaryl C₁₋₆ alkyl, optionally substituted aryloxy, optionally substituted heteroaryloxy, optionally substituted aryl C₁₋₆ alkoxy, or optionally substituted heteroaryl C₁₋₆ alkoxy, wherein said substituent on the aryl or heteroaryl group is one or more group chosen from, hydroxy, mercapto, amino, nitro, halogen atoms, C₁₋₆ alkyl, C₁₋₆ alkoxy, C₁₋₆ alkylthio, or carboxy, wherein R⁵ is a 3- to 8- membered heterocyclic group containing at least one heteroatom chosen from N, O, or S, which is optionally substituted by R⁶, wherein said R⁶H, C₁₋₆ alkyl, halo-C₁₋₆ alkyl, or hydroxy-C₁₋₆ alkyl.

13. A pharmaceutical composition comprising a pharmaceutically effective amount of a compound of general formula (I) or a pharmaceutically acceptable salt thereof according to claim 1, and one or more pharmaceutically acceptable excipients or additives.

14. The preparation method of the compounds of general formula (I) or pharmaceutically acceptable salts thereof according to claim 1, comprising:

reacting a compound of formula (IV) and HNR³R⁴ via acetalization to obtain a compound of formula (II),

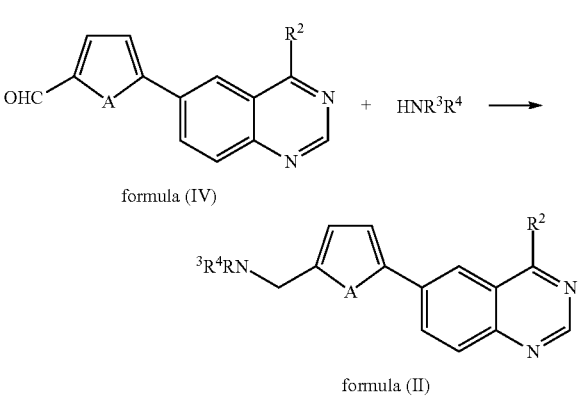

reacting a compound of formula (V) and a compound formula (VI) via acetalization;
removing one molecule of water to obtain a corresponding imine; and
reducing the imine to obtain a compound of formula (III),

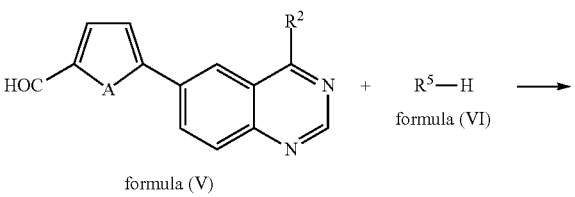

-continued

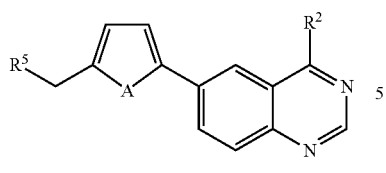

formula (III)

wherein $R^1$-$R^5$ and A are defined according to claim 1, and wherein compounds of general formula (I) comprise compounds of formula (II) and compounds of formula (III).

15. The preparation method according to claim 14, wherein the compound of formula (IV) has formula (IV-1) or formula (IV-2), or the compound of formula (II) has formula (II-1) or formula (II-2), or the compound of formula (III) has formula (III-1), wherein the compound of formula (II-1) is produced by reacting the compound of formula (IV-1) with $HNR^3R^4$:

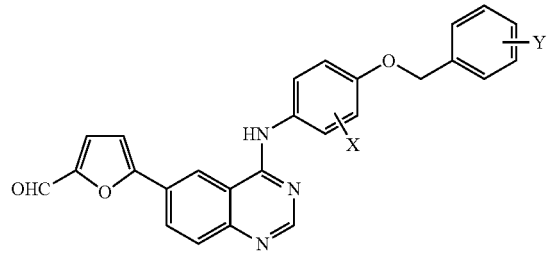

formula (IV-1)

$HNR^3R^4 \longrightarrow$

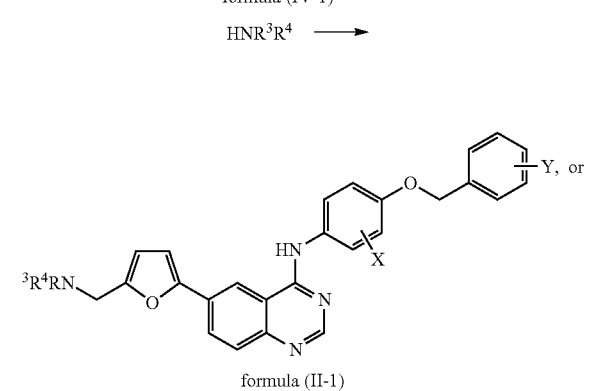

formula (II-1)

wherein the compound of formula (II-1) is produced according to the following steps:

-continued

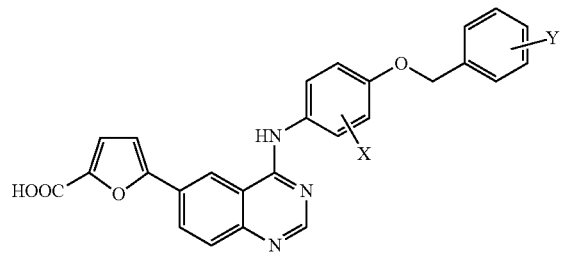

+

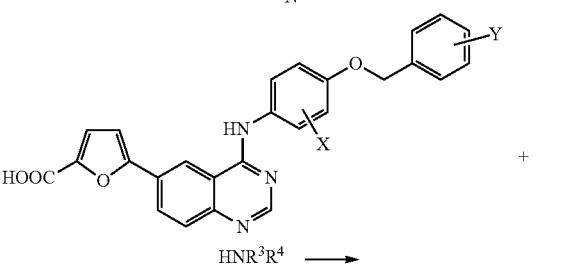

$HNR^3R^4 \longrightarrow$

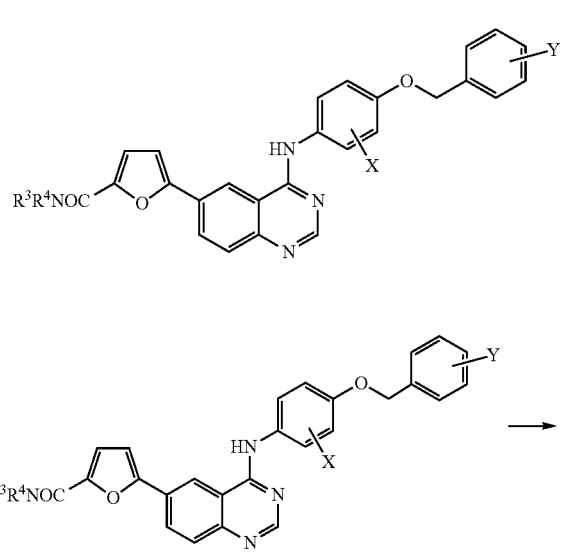

$\longrightarrow$ wherein the compound of formula (II-2) is produced by reacting the compound of formula (IV-2) with $HNR^3R^4$:

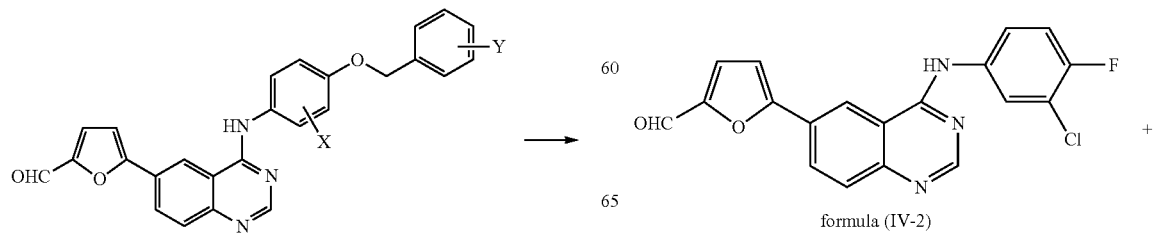

formula (IV-2)

-continued

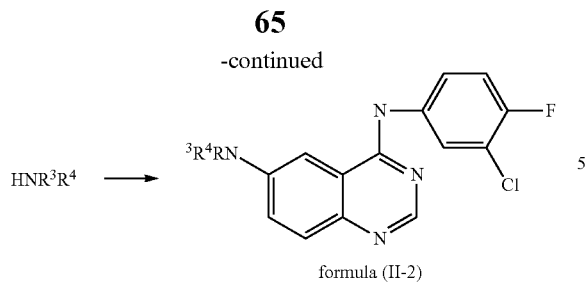

formula (II-2)

wherein the compound of formula (III-I) is produced by reacting a compound of formula (V) with a compound of formula (VI-1):

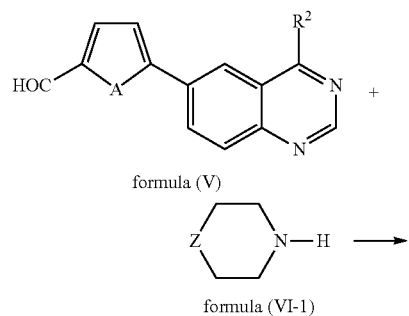

formula (V)

formula (VI-1)

-continued formula (III-1)

wherein X, Y and Z are defined according to claim 1.

16. A method of treating human lung cancers, comprising administering a pharmaceutically effective amount of a compound of general formula (I) or a pharmaceutically acceptable salt thereof according to claim 1 to a subject in need of such treatment.

17. The-method according to claim 16, wherein said human lung cancers are associated with the overexpression and/or overactivity of epidermal growth factor receptor family.

18. A method of treating diseases human lung cancers related to the overexpression and/or overactivity of EGFRI, c-ErbB2/HER2, c-ErbB3/HER3 and c-ErbB4/HER4, and also vascular epidermal growth factor VEGFR in epidermal growth factor receptor family, comprising administering a pharmaceutically effective amount of a compound of general formula (I) or a pharmaceutically acceptable salt thereof according to claim 1 to a subject in need of such treatment.

* * * * *